US007196244B1

(12) United States Patent
Bessereau et al.

(10) Patent No.: US 7,196,244 B1
(45) Date of Patent: Mar. 27, 2007

(54) METHOD OF TRANSPOSON-MEDIATED MUTAGENESIS IN THE NEMATODE CAENORHABDITIS ELEGANS

(75) Inventors: Jean-Louis Bessereau, Paris (FR); Erik M. Jorgensen, Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 171 days.

(21) Appl. No.: 09/980,644

(22) PCT Filed: Jun. 1, 2000

(86) PCT No.: PCT/US00/40091

§ 371 (c)(1),
(2), (4) Date: Nov. 1, 2001

(87) PCT Pub. No.: WO00/73510

PCT Pub. Date: Dec. 7, 2000

Related U.S. Application Data

(60) Provisional application No. 60/136,972, filed on Jun. 1, 1999.

(51) Int. Cl.
*A01K 67/033* (2006.01)
*C12N 15/09* (2006.01)

(52) U.S. Cl. .......................... 800/21; 800/13; 435/440; 435/455

(58) Field of Classification Search ............. 435/320.1; 800/13, 21
See application file for complete search history.

(56) References Cited

U.S. PATENT DOCUMENTS 6,051,430 A 4/2000 Plasterk et al. ............. 435/462

6,489,458 B2* 12/2002 Hackett et al. ............ 536/23.2

FOREIGN PATENT DOCUMENTS

WO WO 00/073510 A1 12/2000

OTHER PUBLICATIONS

Bessereau et al. Nature 413:70-74, 2001.*
Van Leunen et al2. The EMBO Journal 12:2513-2520, 1993.*
Gallegos et al. The EMBO Journal 17:6337-6347, 1998.*
Fukushige, Tetsunari, et al., "Modulation of Gene Expression in the Embryonic Digestive Tract of C. Elegans." Developmental Biology, 178, 1996, Article No. 0218, 276-288.
Gruidl, M.E., et al., "Multiple Potential Germ-line Helicases are Components of the Germ-Line-Specific P granules of Caenorhabditis Elegans," Proc. Natl., Acad. Sci. USA 93, 1996, 13837-42.
Plasterk, Ronald, H. A. et al., "Targeted Alterations of the Caenohabditis Elegans Genome By Transgene instructed DNA Double Strand Break Repair Following Tc1 Excision," The EMBO Journal vol. 11, No. 1, 1992, 287-80.
Plasterk, Ronald H.A., et al., "Reverse Genetics of Caenorhabditis Elegans," BioEssays, vol. 14, No. 9, Sep., 1992, 629-633.
Van Luenen Henri G.A.M., et al. "The Mechanism of Transposition of Tc3 in C. Elegans," Cell, vol. 79, Oct. 21, 2994, 293-301.

(Continued)

*Primary Examiner*—Scott D. Priebe
(74) *Attorney, Agent, or Firm*—TraskBritt

(57) ABSTRACT

The present invention provides methods for generating and identifying mutations in *Caenorhabditis elegans*. Disclosed herein are methods for introducing DNA into the *C. elegans* germline, methods for expressing DNA in the *C. elegans* germline, and methods for generating *C. elegans* mutants by using controlled mobilization of endogenous and heterologous transposons. Also disclosed are a transgene construct for expression in *C. elegans* and methods for inserting single copy DNA sequences into the *C. elegans* germline, and engineering mutations into the *C. elegans* genome.

24 Claims, 9 Drawing Sheets

OTHER PUBLICATIONS

Figure 1:
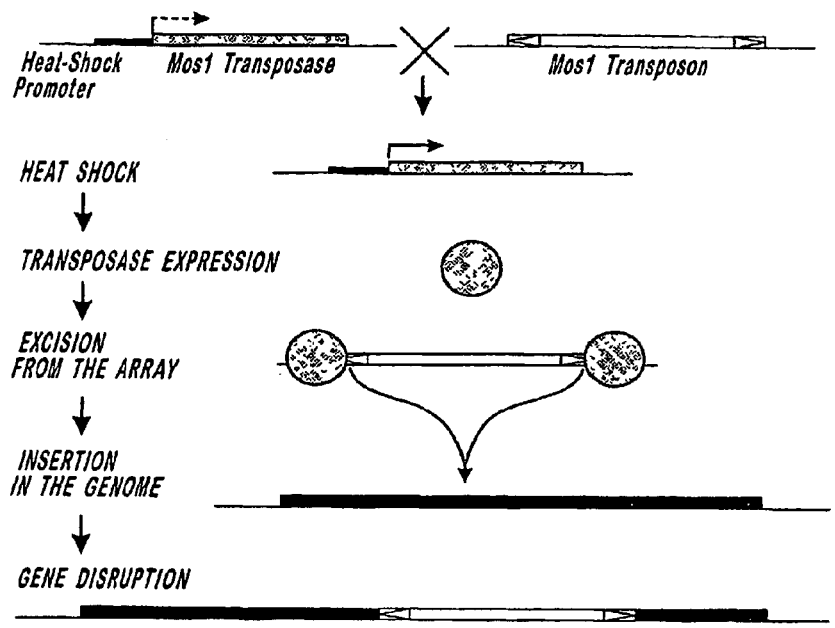

Vos, Jan C., et al. "Transposase is the only Nematode Protein Required for in Vitro Transposition of Tc1," Genes & Development 10, 1996, 755-61.

Kelly et al., Distinct Requirements for Somatic and Germline Expression of a Generally Expressed *Caernorhabditis elegans* Gene, Genetics, May 1997, pp. 227-238.

Gueiros-Filho et al., Trans-kingdom Transposition of the Drosphila Element mariner Within the Protozoan Leishmania, Science, Jun. 13, 1997, pp. 1716-1719, vol. 276.

Hartl et al., Modern Thoughts of an Ancyent Marinere: Function, Evolution, Regulation, Annu. Rev. Genet. 1997, pp. 337-358, vol. 31.

Collins et al., Activation of a transposable element in the germ line but not the soma of *Caenorhadbitis elegans*, Nature, 1987, pp. 726-728, vol. 328.

Jareborg et al., Comparative Analysis of Noncoding Regions of 77 Orthologous Mouse and Human Gene Pairs, Genome Research, 1999, pp. 815-824, vol. 9.

Navarro et al., cgh-1, a conserved predicted RNA helicase required for gametogenesis and protection from physiological germline apoptosis in *C. elegans*, Development, 2001, pp. 3221-3232, vol. 128.

Pesole et al., UTRdb and UTRsite: specialized databases of sequences and functional elements of 5' and 3' untranslated regions of eukaryotic mRNAs, Nucleic Acids Research, 2000, pp. 193-196, vol. 28, No. 1.

Wickens et al., Life and death in the cytoplasm: messages from the 3' end, Current Opinion in Genetics & Development, 1997, pp. 220-232, vol. 7.

Zhang et al., A conserved RNA-binding protein that regulates sexual fates in the *C. elegans* hemaphrodite germ line, Nature, Dec. 4, 1997, pp. 477-484, vol. 390.

Bamber et al., "The *Caenorhabditis elegans* unc-49 Locus Encodes Multiple Subunits of a Heteromultimeric GABA Receptor," J. Neurosci. 19: 5348-5359 (1999).

Bellen et al., "P-element-mediated enhancer detection: a versatile method to study development in *Drosophila*," Genes Dev. 3: 1288-1300 (1989).

Bryan et al., "Insertion and Excision of the Transposable Element mariner in Drosophila," Genetics 125: 103-114 (1990).

Clark et al., "The *Caenorhabditis elegans* Locus lin-15, a Negative Regulator of a Tyrosine Kinase Signaling Pathway, Encodes Two Different Proteins," Genetics 137: 987-997 (1994).

Coates et al., "Mariner transposition and transformation of the yellow fever mosquito, *Aedes aegypil*," Proc. Natl. Acad. Sci. USA 95: 3748-3751 (1998).

Colleaux et al., "Universal Code Equivalent of a Yeast Mitochondrial Intron Reading Frame Is Expressed into *E. coli* as a Specific Double Strand Endonuclease," Cell 44: 521-533 (1986).

Cooley et al., "Insertional Mutagenesis of the *Drosophila* Genome with Single P Elements," Science 239: 1121-1128 (1988).

Coulson et al., "Toward a physical map of the genome of the nematode *Caenorhabditis elegans*," Proc. Natl. Acad. Sci. USA 83: 7821-7825 (1986).

Coulson et al., "YACs and the *C. elegans* Genome," BioEssays 13: 413-417 (1991).

Eide et al., "Insertion and Excision of *Caenorhabditis elegans* Transposable Element Tcl," Mol. Cell. Biol. 8: 737-746 (1988).

Evan et al., "A Matter of Life and Cell Death," Science 281: 1317-1322 (1998).

Fadool et al., "Transposition of the mariner element from *Drosophila manuitiana* in zebrafish," Proc. Natl. Acad. Sci. USA 95: 5182-5186 (1998).

Fire et al., "A modular set of lacZ fusion vectors for studying gene expression in *Caenorhabditis elegans*," Gene 93: 189-198 (1990).

Garza et al., "Introduction of the Transposable Element mariner into the Gemline of *Drosophila melanogaster*," Genetics 128: 303-310 (1991).

Golic, "Generating mosaics by site-specific recombination," D.A. Hartley, ed., Oxford Univ. Press, pp. 1-31 (1993).

Gossen et al., "Tight control of gene expression in mammalian cells by tetracycline-responsive promoters," Proc. Natl. Acad. Sci. USA 89: 5547-5551 (1992).

Jacobson et al., "Molecular structure of a somatically unstable transposable element in *Drosophila*," Proc. Natl. Acad. Sci. USA 83: 8684-8688 (1986).

Kramer et al., "The *Caenorhabditis elegans* rol-6 Gene, Which Interacts with the sqt-I Collagen Gene To Determine Organismal Morphology, Encodes a Collagen," Mol. Cell. Biol. 10: 2081-2089 (1990).

Lampe et al., "A purified mariner transposase is sufficient to mediate transposition in vitro," EMBO J 15: 5470-5479 (1996).

Lohe et al., "Germline Transformation of *Drosophila virilis* With the Transposable Element mariner," Genetics 143: 365-374 (1996).

Lohe et al., "Self-Inflicted Wounds, Template-Directed Gap Repair and a Recombination Hotspot: Effects of the mariner Transposase," Genetics 154: 647-656 (2000).

Loukeris et al., "Introduction of the transposable element Minos into the germ line of *Drosophila melanogaster*," Proc Natl. Acad. Sci. USA 92: 9485-9489 (1995).

Medhora et al., "Molecular and Functional Analysis of mariner Mutator Element Mos I in Drosophilia," Genetics 128: 311-318 (1991).

Mello et al., "Efficient gene transfer in *C. elegans*: extrachromosomal maintenance and integration of transforming sequences," EMBO J 10: 3959-3970 (1991).

Plasterk et al., "Resident aliens, the Tc1/mariner superfamily of transposable elements," Trends Genet. 15: 326-332 (1999).

Plasterk et al., "Transposons," Cold Spring Harbor Laboratory Press, New York, 97-116 (1997).

Robertson et al., "Recent Horizontal Transfer of a mariner Transposable Element among and between Diptera and Neuroptera," Mol. Biol. Eval. 12: 850-862 (1995).

Rushforth et al., "Site-Selected Insertion of the Transposon Tcl into a *Caenorhabditis elegans* Myosin Light Chain Gene," Mol. Cell. Biol. 13: 902-910 (1993).

Rushforth et al., "Splicing Removes the *Caenorhabditis elegans* Transposon Tcl from Most Mutant Pre-mRNAs," Mol. Cell. Biol. 16: 422-429 (1996).

Sanger Center, "*Caenorhabditis* Genome Sequencing Projects," web site at http://www.sanger.ac.uk/Projects/C_elegans/ (date unknown).

Sedensky et al., "Identification of a mariner-like repetitive sequence in *C. elegans*," Nucleic Acids Res. 22: 1719-1723 (1994).

Spradling et al., "Transposition of Cloned P Elements into *Drosophila* Germ Line Chromosomes," Science 218: 341-347 (1982).

Sundararajan et al., "Transposable element interactions in insects: crossmobilization of hobo and Hermes," Insect Mol. Biol. 8: 359-368 (1999).

The C. Elegans Sequencing Consortium, "Genome Sequence of the Nematode *C. elegans*: A Platform for Investigating Biology," Science 282: 2012-2018 (1998).

Tosi et al., "cis and trans factors affecting MosI mariner evolution and transposition in vitro, and its potential for functional genomics," Nucleic Acids Res. 28: 784-790 (2000).

Watson et al., "Movable Genes," Recombinant DNA 175-190, 439-440 2d. ed. (1996).

Wilson et al., "2.2 Mb of contiguous nucleotide sequence from chromosome III of *C. elegans*," Nature 368: 32-38 (1994).

Wood, "Introduction to *C. elegans* Biology," Cold Spring Harbor Laboratory, 1-16 (1988).

Zwaal et al., "Target-selected gene inactivation in Caenorhabditis elegans by using a frozen transposon insertion mutant bank," Proc. Natl. Acad. Sci. USA 90: 7431-7435 (1993).

Zwaal et al., "Two Neuronal G Proteins are Involved in Chemosensation of the *Caenorhabditis elegans* Dauer-Inducing Pheromone," Genetics 145: 715-727 (1997).

\* cited by examiner (Most left end)

CAGTCAAGGTTGACACTTACAAGGTCAAAGTTTATGACAATGATAAATATTTACGTT

TGCGAGACATCTATATGTTCGAACCGACATTCCCTACTTGTACACCTGGtaaatgaaag ctggtgacgtggagattacgtcccccgtaaaaattattgcgaaatatgcaacggtggccg agaaatccgcgaccccgtcgacccagacacggttgattctccagtgacggtcgatcAA

CAAAAAAGATCCATTTTCATCTCCAGTAAGCGATACGATGCAAAAAGACTTCCTTTTG

TATCGTGAAAGCAAAATTCGCATGTGTTTTTGCGCCTCTCCATCTGCCTCT

Fig. 4

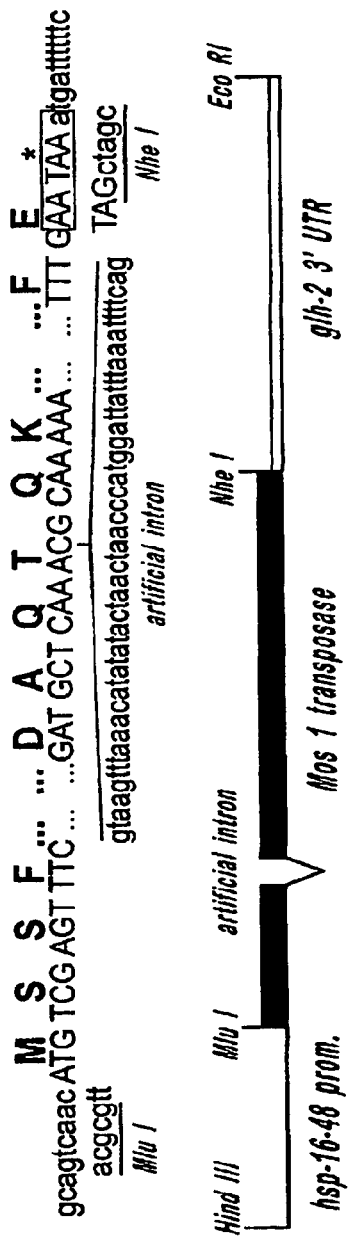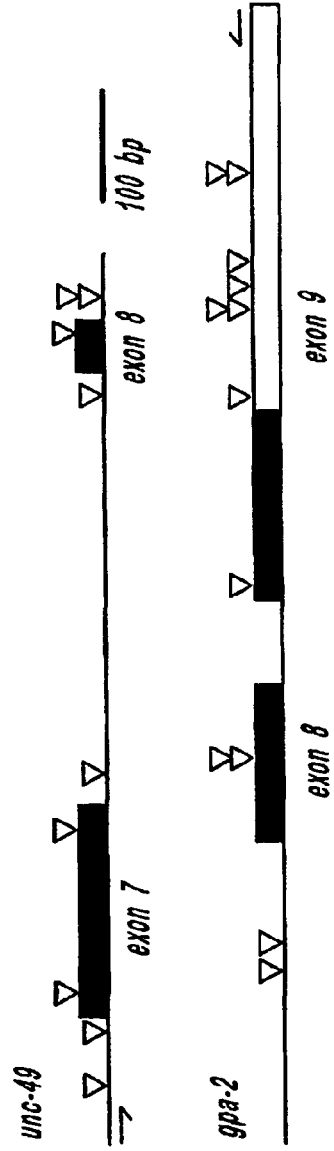
Fig. 5A
Fig. 5B

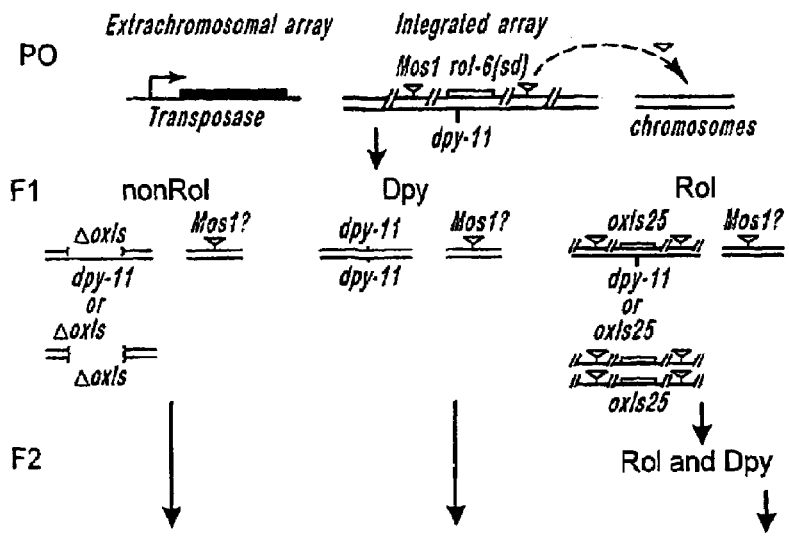

Fig. 6A

| Exp'n vector | Exp. | nonRol/ Rols+nonRol | Insertions/ nonRol | Insertions/ F1 Dpys | dpy-11 oxIs Recomb./ F1 Dpys | Insertions/ F2 Dpys | dpy-11 oxIs Recomb./ F2 Dpys |
|---|---|---|---|---|---|---|---|
| none | | 3/691 0.43% | ND | ND | 0/92 0% | ND | ND |
| glh-2 | #1 | 541/4078 13.3% | 2/188 1.1% | ND | | ND | |
| | #2 | 138/651 21.2% | ND | 2/39 5% | 0/39 0% | 2/17 11% | 2/19 10% |
| | #3 | 250/1191 20.8% | 0/39 0% | 0/35 0% | 2/37 5% | 7/25 28% | 2/27 7% |
| | total | 929/5920 15.7% | 2/227 0.9% | 2/74 3% | 2/76 3% | 9/42 21% | 4/46 9% |
| hsp | #1 | 4/1048 0.38%* | ND | ND | | 6/24 25% | 4/24 17% |
| | #2 | 0/41 0.00%* | ND | 0/13 0% | 0/13 0% | 4/17 23% | 0/17 0% |
| | #3 | 1/140 0.71%* | ND | 7/20 35% | 1/20 5% | 8/20 40% | 3/20 15% |
| | total | 5/1229 0.41%* | ND | 7/33 21% | 1/33 3% | 18/61 30% | 7/61 11% |

* number of nonRol progeny does not significantly differ from control lacking a transposase expressing construct (3/691, 0.43%).

Fig. 6B

```
oxTi1   GTTTAGGGACGAGTGACATAccaggtgtac........gtacacctgaTAATTCTCCGAAAGCTTCAG
oxTi2   TCGATAAATAAATTATTTTAccaggtgtac........gtacacctgaTAATTCTATCCAAAAATCGC
oxTi3   AAAGTAGTGGATGCGATATAccaggtgtac........gtacacctgaTAATAAGAGAGGCGAAGGAT
oxTi4   TCCTCTTTTCCAGACGAGTAccaggtgtac........gtacacctgaTATATCCTTTTGTTCCTTGC
oxTi5   GTCGGACAATCAGAAGTGTAccaggtgtac........gtacacctgaTAAGAACTAAAAGGACACCG
oxTi6   TTGAACAATAAATACTAATAccaggtgtac........gtacacctgaTATTGTTGTCCTCAAGATTT
oxTi8   GACGCAATAAATCCACAATAccaggtgtac........gtacacctgaTAATTTTCCCGACTCTTACA
oxTi9   CCCTCTCCAATAGTCTAGTAccaggtgtac........gtacacctgaTAAATGTCATCAGAATTCAT
oxTi11  ACCAAAAGCAAAAACACTTAccaggtgtac........gtacacctgaTAACCAAATGATGGGTGGCA
```

*Fig. 7C*

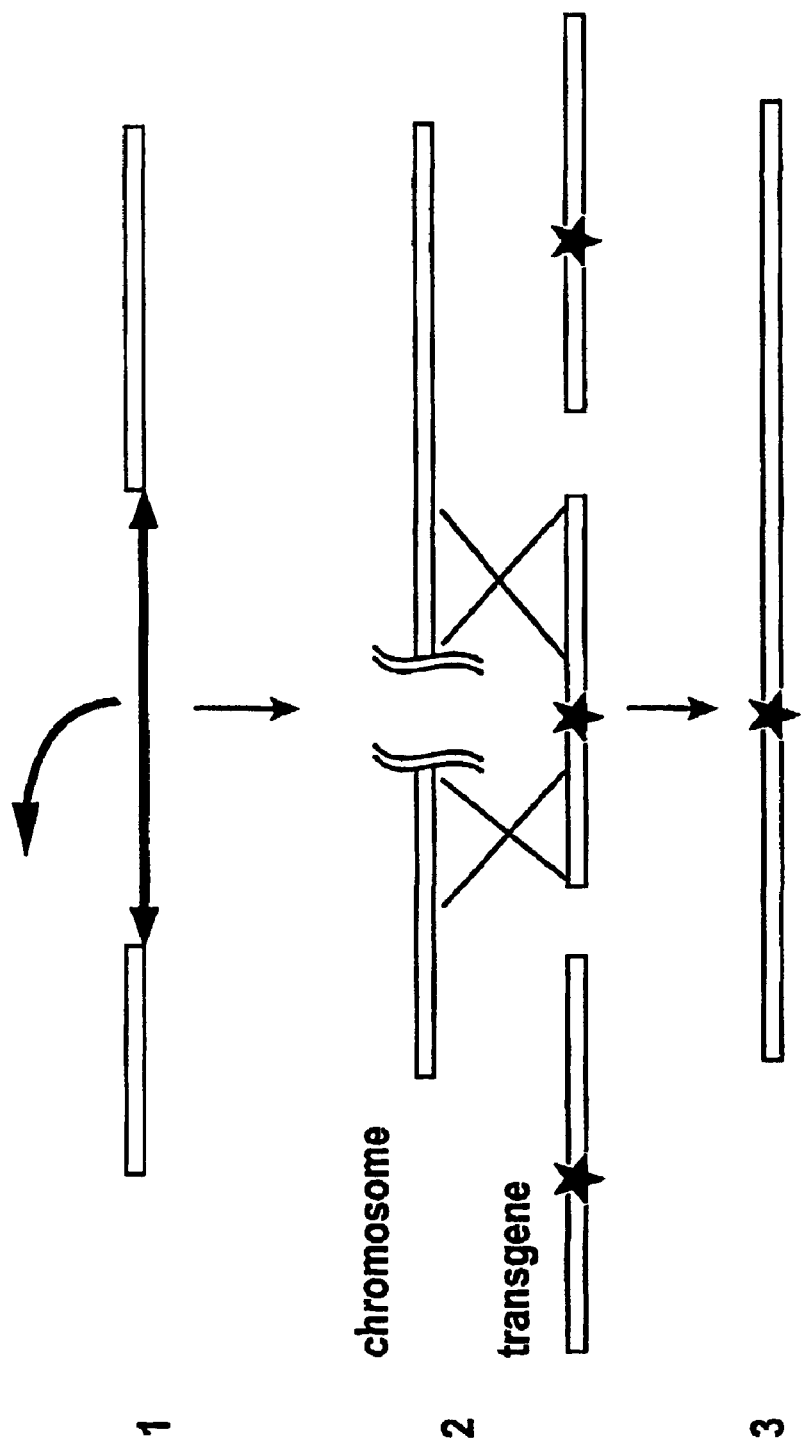

SEQUENCE LISTING

```
<160> NUMBER OF SEQ ID NOS: 56

<210> SEQ ID NO 1
<211> LENGTH: 26
<212> TYPE: DNA
<213> ORGANISM: Artificial
<220> FEATURE:
<223> OTHER INFORMATION: Primer oJL102

<400> SEQUENCE: 1
caaccttgac tgtcgaacca ccatag                                              26

<210> SEQ ID NO 2
<211> LENGTH: 23
<212> TYPE: DNA
<213> ORGANISM: Artificial
<220> FEATURE:
<223> OTHER INFORMATION: Primer oJL104

<400> SEQUENCE: 2
acaaagagcg aacgcagacg agt                                                 23

<210> SEQ ID NO 3
<211> LENGTH: 25
<212> TYPE: DNA
<213> ORGANISM: Artificial
<220> FEATURE:
<223> OTHER INFORMATION: Primer oJL103

<400> SEQUENCE: 3
tctgcgagtt gtttttgcgt ttgag                                               25

<210> SEQ ID NO 4
<211> LENGTH: 18
<212> TYPE: DNA
<213> ORGANISM: Artificial
<220> FEATURE:
<223> OTHER INFORMATION: Primer oJL88

<400> SEQUENCE: 4
cgcatgcggc ttactcac                                                       18

<210> SEQ ID NO 5
<211> LENGTH: 22
```

-continued

```
<212> TYPE: DNA
<213> ORGANISM: Artificial
<220> FEATURE:
<223> OTHER INFORMATION: Primer oJL89

<400> SEQUENCE: 5
ggccccatcc gattaccacc ta                                              22

<210> SEQ ID NO 6
<211> LENGTH: 21
<212> TYPE: DNA
<213> ORGANISM: Artificial
<220> FEATURE:
<223> OTHER INFORMATION: Primer oJL19

<400> SEQUENCE: 6
gcgaaacgca taccaactgt a                                               21

<210> SEQ ID NO 7
<211> LENGTH: 21
<212> TYPE: DNA
<213> ORGANISM: Artificial
<220> FEATURE:
<223> OTHER INFORMATION: Primer oJL20

<400> SEQUENCE: 7
ttcatgccga aaagcaggcg t                                               21

<210> SEQ ID NO 8
<211> LENGTH: 21
<212> TYPE: DNA
<213> ORGANISM: Artificial
<220> FEATURE:
<223> OTHER INFORMATION: Primer oJL132

<400> SEQUENCE: 8
atatgcggtg cgatgggtga g                                               21

<210> SEQ ID NO 9
<211> LENGTH: 22
<212> TYPE: DNA
<213> ORGANISM: Artificial
<220> FEATURE:
<223> OTHER INFORMATION: Primer oJL133

<400> SEQUENCE: 9
ggcgaacgcg atgagaagaa ag                                              22

<210> SEQ ID NO 10
<211> LENGTH: 26
<212> TYPE: DNA
<213> ORGANISM: Artificial
<220> FEATURE:
<223> OTHER INFORMATION: Primer oJL114

<400> SEQUENCE: 10
aaagattcag aaggtcggta gatggg                                          26

<210> SEQ ID NO 11
<211> LENGTH: 22
<212> TYPE: DNA
<213> ORGANISM: Artificial
<220> FEATURE:
<223> OTHER INFORMATION: Primer oJL115

<400> SEQUENCE: 11
```
gctcaattcg cgccaaacta tg                                              22

<210> SEQ ID NO 12
<211> LENGTH: 24
<212> TYPE: DNA
<213> ORGANISM: Artificial
<220> FEATURE:
<223> OTHER INFORMATION: Primer oJL116

<400> SEQUENCE: 12
gaacgagaga ggcagatgga gagg                                            24

<210> SEQ ID NO 13
<211> LENGTH: 21
<212> TYPE: DNA
<213> ORGANISM: Artificial
<220> FEATURE:
<223> OTHER INFORMATION: Primer oJL129

<400> SEQUENCE: 13
ccaaatgcgt ctgtcccact c                                               21

<210> SEQ ID NO 14
<211> LENGTH: 24
<212> TYPE: DNA
<213> ORGANISM: Artificial
<220> FEATURE:
<223> OTHER INFORMATION: Primer oJL149

<400> SEQUENCE: 14
aagtatggcc aaacgacccg acac                                            24

<210> SEQ ID NO 15
<211> LENGTH: 23
<212> TYPE: DNA
<213> ORGANISM: Artificial
<220> FEATURE:
<223> OTHER INFORMATION: primer oJL150

<400> SEQUENCE: 15
gcattggcac ctttctccct tct                                             23

<210> SEQ ID NO 16
<211> LENGTH: 21
<212> TYPE: DNA
<213> ORGANISM: Artificial
<220> FEATURE:
<223> OTHER INFORMATION: primer oJL145

<400> SEQUENCE: 16
acaggcagca ttttgtagtc t                                               21

<210> SEQ ID NO 17
<211> LENGTH: 24
<212> TYPE: DNA
<213> ORGANISM: Artificial
<220> FEATURE:
<223> OTHER INFORMATION: primer oJL148

<400> SEQUENCE: 17
aggctgcctc gtaagttcct acag                                            24

<210> SEQ ID NO 18
<211> LENGTH: 51
<212> TYPE: DNA
<213> ORGANISM: Artificial

<220> FEATURE:
<223> OTHER INFORMATION: artificial intron

<400> SEQUENCE: 18
gtaagtttaa acatatatac taactaaccc atggattatt taaattttca g        51

<210> SEQ ID NO 19
<211> LENGTH: 26
<212> TYPE: DNA
<213> ORGANISM: Artificial
<220> FEATURE:
<223> OTHER INFORMATION: primer oJL21

<400> SEQUENCE: 19
cgaagcttgc tggacggaaa tagtgg                                    26

<210> SEQ ID NO 20
<211> LENGTH: 26
<212> TYPE: DNA
<213> ORGANISM: Artificial
<220> FEATURE:
<223> OTHER INFORMATION: primer oJL22

<400> SEQUENCE: 20
cgacgcgttc ttgaagttta gagaat                                    26

<210> SEQ ID NO 21
<211> LENGTH: 34
<212> TYPE: DNA
<213> ORGANISM: Artificial
<220> FEATURE:
<223> OTHER INFORMATION: primer oJL77

<400> SEQUENCE: 21
gcacgcgtta tgtcgagttt cgtgccgaat aaag                           34

<210> SEQ ID NO 22
<211> LENGTH: 49
<212> TYPE: DNA
<213> ORGANISM: Artificial
<220> FEATURE:
<223> OTHER INFORMATION: primer oJL78

<400> SEQUENCE: 22
gcgctagcta ttcaaagtat tgccgtcgc tcgcgacaca ttttttccca           49

<210> SEQ ID NO 23
<211> LENGTH: 347
<212> TYPE: DNA
<213> ORGANISM: Artificial
<220> FEATURE:
<223> OTHER INFORMATION: inverse PCR product

<400> SEQUENCE: 23
cagtcaaggt tgacacttac aaggtcaaag ttttatgaca atcgataaat atttacgttt    60
gcgagacatc tatatgttcg aaccgacatt ccctacttgt acacctggta aatgaaagct   120
ggtgacgtgg agattacgtc cccgtaaaaa ttattgcgaa atatgcaacg gtggccgaga   180
aaatccgcga ccccgtcgac ccagacacgg ttgattctcc agtgacggtc gatcaacaaa   240
aaagatccat ttttcatctc cagtaacgat acgatgcaaa aacgacttcc ttttgtatcg   300
tgaaagcaaa atttcgcatg tgttttttgcg cctctccatc tgcctct              347

<210> SEQ ID NO 24

```
<211> LENGTH: 21
<212> TYPE: DNA
<213> ORGANISM: Drosophila mauritiana

<400> SEQUENCE: 24
gcagtcaaca tgtcgagttt c                                              21

<210> SEQ ID NO 25
<211> LENGTH: 18
<212> TYPE: DNA
<213> ORGANISM: Drosophila mauritiana

<400> SEQUENCE: 25
gatgctcaaa cgcaaaaa                                                  18

<210> SEQ ID NO 26
<211> LENGTH: 20
<212> TYPE: DNA
<213> ORGANISM: Drosophila mauritiana

<400> SEQUENCE: 26
tttgaataaa tgattttttc                                                20

<210> SEQ ID NO 27
<211> LENGTH: 4
<212> TYPE: PRT
<213> ORGANISM: Drosophila mauritiana

<400> SEQUENCE: 27

Met Ser Ser Phe
1

<210> SEQ ID NO 28
<211> LENGTH: 6
<212> TYPE: PRT
<213> ORGANISM: Drosophila mauritiana

<400> SEQUENCE: 28

Asp Ala Gln Thr Gln Lys
1               5

<210> SEQ ID NO 29
<211> LENGTH: 30
<212> TYPE: DNA
<213> ORGANISM: Artificial
<220> FEATURE:
<223> OTHER INFORMATION: oxTi1 insertion of Mos1 into C. Elegans genome

<400> SEQUENCE: 29
gtttagcgac gagtgacata ccaggtgtac                                     30

<210> SEQ ID NO 30
<211> LENGTH: 30
<212> TYPE: DNA
<213> ORGANISM: Artificial
<220> FEATURE:
<223> OTHER INFORMATION: oxTi1 insertion of Mos1 into C. Elegans genome

<400> SEQUENCE: 30
gtacacctga taattctccg aaagcttcag                                     30

<210> SEQ ID NO 31
<211> LENGTH: 30
<212> TYPE: DNA
<213> ORGANISM: Artificial
```

```
<220> FEATURE:
<223> OTHER INFORMATION: oxTi2 insertion of Mos1 into C. Elegans genome

<400> SEQUENCE: 31
tcgataaata aattatttta ccaggtgtac                                30

<210> SEQ ID NO 32
<211> LENGTH: 30
<212> TYPE: DNA
<213> ORGANISM: Artificial
<220> FEATURE:
<223> OTHER INFORMATION: oxTi2 insertion of Mos1 into C. Elegans genome

<400> SEQUENCE: 32
gtacacctga taattctatc caaaaatcgc                                30

<210> SEQ ID NO 33
<211> LENGTH: 30
<212> TYPE: DNA
<213> ORGANISM: Artificial
<220> FEATURE:
<223> OTHER INFORMATION: oxTi3 insertion of Mos1 into C. Elegans genome

<400> SEQUENCE: 33
aaagtagtgg atgcgatata ccaggtgtac                                30

<210> SEQ ID NO 34
<211> LENGTH: 30
<212> TYPE: DNA
<213> ORGANISM: Artificial
<220> FEATURE:
<223> OTHER INFORMATION: oxTi3 insertion of Mos1 into C. Elegans genome

<400> SEQUENCE: 34
gtacacctga taataagaga ggcgaaggat                                30

<210> SEQ ID NO 35
<211> LENGTH: 30
<212> TYPE: DNA
<213> ORGANISM: Artificial
<220> FEATURE:
<223> OTHER INFORMATION: oxTi4 insertion of Mos1 into C. Elegans genome

<400> SEQUENCE: 35
tcctcttttc cagacgagta ccaggtgtac                                30

<210> SEQ ID NO 36
<211> LENGTH: 30
<212> TYPE: DNA
<213> ORGANISM: Artificial
<220> FEATURE:
<223> OTHER INFORMATION: oxTi4 insertion of Mos1 into C. Elegans genome

<400> SEQUENCE: 36
gtacacctga tatatccttt tgttccttgc                                30

<210> SEQ ID NO 37
<211> LENGTH: 30
<212> TYPE: DNA
<213> ORGANISM: Artificial
<220> FEATURE:
<223> OTHER INFORMATION: oxTi5 insertion of Mos1 into C. Elegans genome

<400> SEQUENCE: 37
gtcggacaat cagaagtgta ccaggtgtac                                30
```

<210> SEQ ID NO 38
<211> LENGTH: 30
<212> TYPE: DNA
<213> ORGANISM: Artificial
<220> FEATURE:
<223> OTHER INFORMATION: oxTi5 insertion of Mos1 into C. Elegans genome

<400> SEQUENCE: 38
gtacacctga taagaactaa aaggacaccg           30

<210> SEQ ID NO 39
<211> LENGTH: 30
<212> TYPE: DNA
<213> ORGANISM: Artificial
<220> FEATURE:
<223> OTHER INFORMATION: oxTi6 insertion of Mos1 into C. Elegans genome

<400> SEQUENCE: 39
ttgaacaata aatactaata ccaggtgtac           30

<210> SEQ ID NO 40
<211> LENGTH: 30
<212> TYPE: DNA
<213> ORGANISM: Artificial
<220> FEATURE:
<223> OTHER INFORMATION: oxTi6 insertion of Mos1 into C. Elegans genome

<400> SEQUENCE: 40
gtacacctga tattgttgtc ctcaagattt           30

<210> SEQ ID NO 41
<211> LENGTH: 30
<212> TYPE: DNA
<213> ORGANISM: Artificial
<220> FEATURE:
<223> OTHER INFORMATION: oxTi8 insertion of Mos1 into C. Elegans genome

<400> SEQUENCE: 41
gacgcaataa atccacaata ccaggtgtac           30

<210> SEQ ID NO 42
<211> LENGTH: 30
<212> TYPE: DNA
<213> ORGANISM: Artificial
<220> FEATURE:
<223> OTHER INFORMATION: oxTi8 insertion of Mos1 into C. Elegans genome

<400> SEQUENCE: 42
gtacacctga taattttccc gactcttaca           30

<210> SEQ ID NO 43
<211> LENGTH: 30
<212> TYPE: DNA
<213> ORGANISM: Artificial
<220> FEATURE:
<223> OTHER INFORMATION: oxTi9 insertion of Mos1 into C. Elegans genome

<400> SEQUENCE: 43
ccctctccaa tagtctagta ccaggtgtac           30

<210> SEQ ID NO 44
<211> LENGTH: 30
<212> TYPE: DNA
<213> ORGANISM: Artificial
<220> FEATURE:
<223> OTHER INFORMATION: oxTi9 insertion of Mos1 into C. Elegans genome

```
<400> SEQUENCE: 44
gtacacctga taaatgtcat cagaattcat                                    30

<210> SEQ ID NO 45
<211> LENGTH: 30
<212> TYPE: DNA
<213> ORGANISM: Artificial
<220> FEATURE:
<223> OTHER INFORMATION: oxTi11 insertion of Mos1 into C. Elegans genome

<400> SEQUENCE: 45
accaaaagca aaaacactta ccaggtgtac                                    30

<210> SEQ ID NO 46
<211> LENGTH: 30
<212> TYPE: DNA
<213> ORGANISM: Artificial
<220> FEATURE:
<223> OTHER INFORMATION: oxTi11 insertion of Mos1 into C. Elegans genome

<400> SEQUENCE: 46
gtacacctga taaccaaatg atgggtggca                                    30

<210> SEQ ID NO 47
<211> LENGTH: 28
<212> TYPE: DNA
<213> ORGANISM: Artificial
<220> FEATURE:
<223> OTHER INFORMATION: oxTi4 insertion of Mos1

<400> SEQUENCE: 47
ctcttttcca gacgagtacc aggtgtac                                      28

<210> SEQ ID NO 48
<211> LENGTH: 27
<212> TYPE: DNA
<213> ORGANISM: Artificial
<220> FEATURE:
<223> OTHER INFORMATION: oxTi4 insertion of Mos1

<400> SEQUENCE: 48
tacacctgat atatcctttt gttcctt                                       27

<210> SEQ ID NO 49
<211> LENGTH: 36
<212> TYPE: DNA
<213> ORGANISM: Artificial
<220> FEATURE:
<223> OTHER INFORMATION: lesion generated after removal of Mos1 in oxTi4
      insertion

<400> SEQUENCE: 49
ctcttttcca gacgagtata tatccttttg ttcctt                             36

<210> SEQ ID NO 50
<211> LENGTH: 37
<212> TYPE: DNA
<213> ORGANISM: Artificial
<220> FEATURE:
<223> OTHER INFORMATION: lesion generated after removal of Mos1 in oxTi4
      insertion

<400> SEQUENCE: 50
ctcttttcca gacgagtaat atatcctttt gttcctt                            37
```

<210> SEQ ID NO 51
<211> LENGTH: 39
<212> TYPE: DNA
<213> ORGANISM: Artificial
<220> FEATURE:
<223> OTHER INFORMATION: lesion generated after removal of Mos1 in oxTi4
      insertion

<400> SEQUENCE: 51
ctcttttcca gacgagtatg atatatcctt ttgttcctt                              39

<210> SEQ ID NO 52
<211> LENGTH: 37
<212> TYPE: DNA
<213> ORGANISM: Artificial
<220> FEATURE:
<223> OTHER INFORMATION: lesion generated after removal of Mos1 in oxTi4
      insertion

<400> SEQUENCE: 52
ctcttttcca gacgagtact atatccttt gttcctt                                 37

<210> SEQ ID NO 53
<211> LENGTH: 21
<212> TYPE: DNA
<213> ORGANISM: Artificial
<220> FEATURE:
<223> OTHER INFORMATION: lesion generated after removal of Mos1 in oxTi4
      insertion

<400> SEQUENCE: 53
tgatatatcc ttttgttcct t                                                 21

<210> SEQ ID NO 54
<211> LENGTH: 17
<212> TYPE: DNA
<213> ORGANISM: Artificial
<220> FEATURE:
<223> OTHER INFORMATION: lesion generated after removal of Mos1 in oxTi4
      insertion

<400> SEQUENCE: 54
ctcttttcca gacgaga                                                      17

<210> SEQ ID NO 55
<211> LENGTH: 18
<212> TYPE: DNA
<213> ORGANISM: Artificial
<220> FEATURE:
<223> OTHER INFORMATION: lesion generated after removal of Mos1 in oxTi4
      insertion

<400> SEQUENCE: 55
ctcttttcca gacgagta                                                     18

<210> SEQ ID NO 56
<211> LENGTH: 66
<212> TYPE: DNA
<213> ORGANISM: Artificial
<220> FEATURE:
<223> OTHER INFORMATION: lesion generated after removal of Mos1 in oxTi4
      insertion

```
-continued

<400> SEQUENCE: 56
ctcttttcca gacgagtaat tgtttactct cagtgcagtc aacatgtcga tatccttttg      60
ttcctt                                                                66
```

METHOD OF TRANSPOSON-MEDIATED MUTAGENESIS IN THE NEMATODE CAENORHABDITIS ELEGANS

CROSS-REFERENCE TO RELATED APPLICATION

This application is a national stage entry of and claims priority under 35 U.S.C. § 365 to PCT/US00/40091, filed Jun. 1, 2000, designating the United States of America, corresponding to PCT International Publication WO 00/073510 (published in English on Dec. 7, 2000), which claims the benefit of U.S. Provisional Application No. 60/136,972, filed Jun. 1, 1999.

1. FIELD OF THE INVENTION

The present invention relates to methods for generating and identifying mutations in the genome of the nematode *Caenorhabditis elegans* (hereinafter "*C. elegans*"). More specifically, the present invention relates to a transgene construct for expression in *C. elegans*, and to methods for regulating mobilization of heterologous or endogenous transposons in the *C. elegans* genome, inserting a heterologous DNA sequence into *C. elegans* germline DNA, and engineering mutations into the *C. elegans* genome.

2. TECHNICAL BACKGROUND

The use of model genetic systems had its beginnings in the earliest days of the science of genetics and, as a result of the tremendous value of such systems in understanding genetic phenomena, continues in the present. Researchers often use in their work organisms which have short life spans, limited space requirements, and relatively small genomes. Specifically, certain species of worms, fruit flies, and yeast cells are common subjects of research. Using such organisms, researchers may learn the function of the various genes found within the DNA of the organisms. One commonly used method is to generate mutations in the genome of an organism, followed by selection or screening for those mutations which confer a specific property or characteristic to the organism. These mutational studies suggest probable functions for the genes in which mutations occur. Mutations often occur when a gene is changed in such a way that the product of the gene is altered or nonfunctional.

A common method for generating mutations uses transposable elements. Transposable elements are segments of DNA which have the ability to "hop"—that is, to be excised from their initial position in the DNA and move to a new location. In doing this, a transposable element, also known as a transposon, may insert into some portion of a gene, thus disrupting or even changing the function of the gene. Further, additional mutations may be created by remobilizing the transposon. Since this remobilization often occurs imperfectly, changes are created in the DNA sequence, leaving the final sequence different from the original sequence. See J. D. Watson, J. Witkowski, M. Gilman, and M. Zoller, *Recombinant DNA* 175–190, 439–440 2d. ed. (1996).

The P element, a transposable element found in the genes of fruit flies, see, e.g., A. C. Spradling, G. M. Rubin, *Science* 218, 341 (1982); J. D. Watson, J. Witkowski, M. Gilman, and M. Zoller, *Recombinant DNA* 175, 177 2d. ed. (1996), has been an enormously useful tool in *Drosophila* genetic analysis for two reasons. First, these transposons have been used for insertional mutagenesis. Mutagenic insertions constitute molecular tags that are used to rapidly clone the mutated gene. L. Cooley, R. Kelley, A. Spradling, *Science* 239, 1121 (1988). Particularly helpful in such studies is the presence of strains that lack any copies of the transposon. Second, P elements are used to introduce single copies of foreign sequences into the host genome. This feature is particularly useful for the rapid identification of gene expression patterns by using enhancer traps. H. J. Bellen, et al., *Genes Dev.* 3, 1288 (1989). The availability of such techniques would be particularly advantageous in studies of the genome of the nematode *C. elegans*.

*C. elegans* is a model system in which genetics can be used to identify genes and biological pathways which are conserved between nematodes and vertebrates, and which thus constitute potential targets for the treatment of various diseases. *C. elegans* is particularly advantageous for genetic studies because it is easily propagated and because the genetic and physical maps of its genome are well-characterized. W. B. Wood, *Introduction to C. elegans Biology* (1988). The characterization of gene structure in *C. elegans* has become routine, largely through the efforts of the *C. elegans* genome project. The workers involved in this effort have cloned the entire genome into cosmid or YAC vectors and have completed the genomic sequence. *C. elegans* Sequencing Consortium, *Science* 282:2012–2018 (1998); A. Coulson et al., *Proc. Natl. Acad. Sci. USA* 83:7821–7825 (1986); A. Coulson et al., *Bioessays* 13:413–417 (1991); R. Wilson et al., *Nature* 368:32–38 (1994).

Standard mutagenesis in *C. elegans* employs chemical mutagens. After generation of a mutant, identification of the gene requires time-consuming genetic mapping followed by single gene rescue. Alternatively, transposon-based mutagenesis has been attempted using mutant backgrounds like mut-2, but efficiency of transposition is low and not specific for a defined transposon class. Further, since the genomes of all *C. elegans* strains contain transposons, it is very difficult to identify relevant insertions. Thus, utility of native transposons for regulated transposition in *C. elegans* is limited. First, all strains contain multiple copies of these transposons and thus new insertions do not provide unique tags. Second, mutator strains tend to activate the transposition of several classes of transposons, so that the type of transposon associated with a particular mutation is not known. Third, transposition is not regulated and the transposon tag can be lost by excision in subsequent generations. Fourth, attempts to regulate transposase expression have failed because expression of transgenes in the germline of *C. elegans* is very difficult. Although one could theoretically regulate the transposition of a specific element by expressing the transposase under the control of a germline-specific promoter, transgenic arrays are typically silenced in the germline. W. G. Kelly, S. Xu, M. K. Montgomery, A. Fire, *Genetics* 146, 227 (1997).

Another problem in this field is the difficulty of expressing DNA in the *C. elegans* germline. Current methods, see, e.g., W. G. Kelly et al., *Genetics* 146:227–238 (1997), are not adequate. First, current methods for expressing foreign DNA in the *C. elegans* germline do not work for all genes. Second, expression of genes introduced using these methods declines over time.

Finally, introduction of single copy DNA is not possible using existing technology.

From the foregoing, it will be appreciated that it would be a significant advancement in the art to provide methods that allow regulated expression of foreign DNA in the *C. elegans* germline. It would be a further advancement to provide methods that allow germline expression of a transgene in *C.*

*elegans*. It would be a further advancement in the art to provide regulated expression of such a transgene in the germline, as by regulation using a heat-shock promoter. It would be a further advancement to provide methods of regulating the transposition of either endogenous or heterologous transposons in *C. elegans*. Further, it would be an advancement to provide transgene constructs to facilitate germline expression of transgenes and regulated transposition of homologous and heterologous transposons. Such compositions of matter and methods are disclosed herein.

3. BRIEF SUMMARY OF THE INVENTION

The present invention relates to improved methods for generating and identifying mutations in *C. elegans*, and includes methods for introducing heterologous DNA into the *C. elegans* germline and causing its expression. In certain embodiments, a method of the present invention comprises the steps of inserting a transgene construct into the *C. elegans*, wherein the construct comprises a heterologous gene operably linked to a promoter and a 3' untranslated region of a gene that is expressed in the *C. elegans* germline; and expressing the heterologous gene. In certain embodiments, this method further comprises the removal of all bacterial plasmid sequences and repeated sequences from the DNA to be introduced. In certain preferred embodiments, a promoter that is active in the *C. elegans* germline drives expression of the transgene. In certain especially preferred embodiments, the promoter is an inducible promoter.

The present invention further relates to a transgene construct for expression in *C. elegans* which comprises a heterologous gene operably linked to a promoter and a 3' untranslated region of a gene expressed in the *C. elegans* genome. In certain embodiments, the transgene construct further comprises a promoter that is active in the germline of *C. elegans* or a promoter that is inducible.

The present invention further relates to methods for generating and identifying mutations in *C. elegans*. In one embodiment, a method of the present invention comprises the introduction and expression of a transposase gene to mobilize either endogenous or heterologous transposons. In certain preferred embodiments, the transposons are endogenous Tc3 transposons.

In certain other embodiments, the transposons are heterologous transposons, such as the *Drosophila* mariner element. Controlled mobilization of heterologous transposons allows the generation of mutations, which are tagged by the insertion of the transposon. PCR-based techniques permit rapid identification of the transposon insertion that caused the mutation.

The present invention further relates to methods for introducing single copy DNA sequences into *C. elegans*. In certain preferred embodiments, a method of the present invention comprises introducing a transposon comprising a heterologous DNA sequence into a *C. elegans*, introducing a transgene construct comprising a transposase gene operably linked to a promoter and a 3' untranslated region of a gene that is expressed in the *C. elegans* germline, and expressing the transposase such that the transposase integrates into a *C. elegans* chromosome as a single copy. The transposon may be engineered to introduce a DNA sequence, such as one that codes for a reporter gene such as, for example, a green fluorescent protein. The introduced DNA sequence may also contain FRT/FLP or CRE/LOX recombination sites. Alternatively, the introduced DNA sequence may contain polyadenylation sites or transcriptional terminators.

These and other features and advantages of the present invention will become more fully apparent from the following detailed description.

4. SUMMARY OF THE DRAWINGS

FIG. 1 schematically depicts a method for mutagenesis by controlled heterologous transposition.

Figure 2:
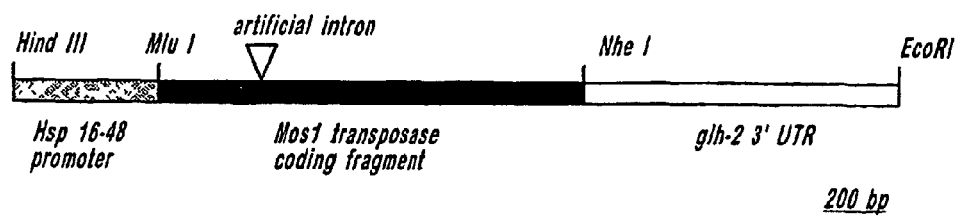

FIG. 2 depicts the structure of the pJL44 Mos1 transposase expression vector.

Figure 3:
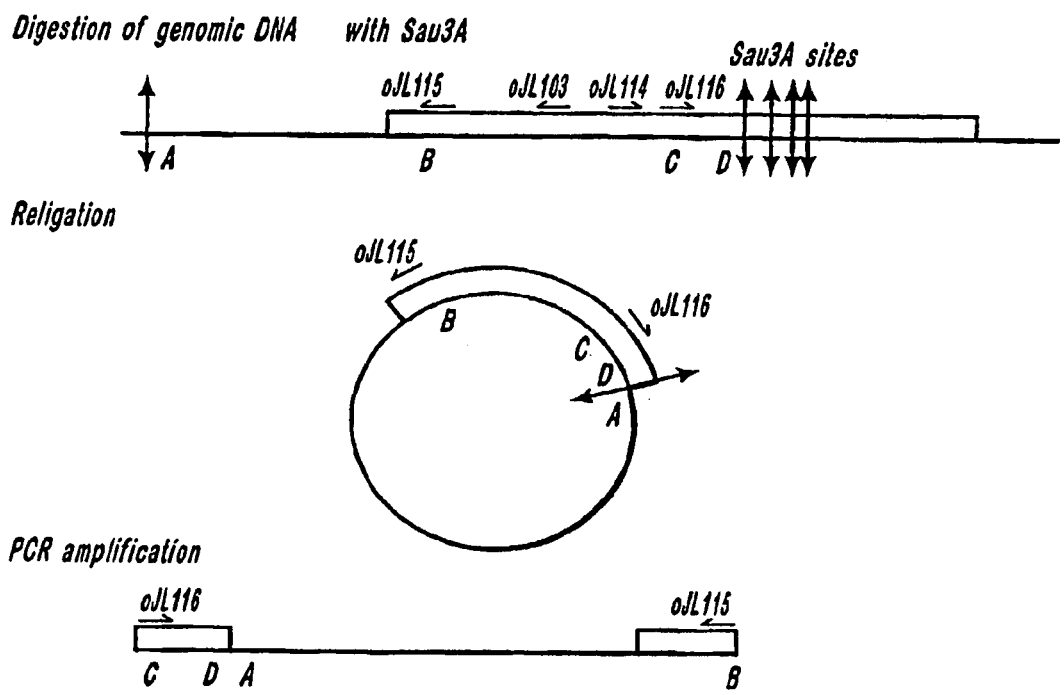

FIG. 3 schematically depicts a method for identifying sequences flanking the Mos1 insertion site using inverse PCR.

FIG. 4 depicts the sequence (SEQ ID NO: 23) of an inverse PCR product. Nucleotides in capital letters are from the Mos1 transposon. The *C. elegans*-flanking genomic region is in lower case. It matches the Y47C4.A sequence from chromosome X available at the Sanger Centre. See the Sanger Centre web site at on the World Wide Web at sanger.ac.uk/Projects/C_elegans/.

FIG. 5 depicts the mobilization of Mos1 in C. elegance somatic cells. (A) Engineering of the Mos transposase encoding sequence. Depicted therein are nucleotides 1–21 (SEQ ID NO:24), 262–279 (SEQ ID NO:25), and 1039–1058 (SEQ ID NO: 26) of the Mos1 gene. Also depicted are the corresponding amino acids 1–4 (SEQ ID NO:27), 85–90 (SEQ ID NO:28), and 344–345 of the Mos1 protein sequence (SEQ ID NO: 25). Restriction sites were generated at the 5' and 3' ends of the coding sequence (new sequence is indicated under the original sequence). The endogenous polyadenylation signal (boxed) was disrupted and an artificial intron (SEQ ID NO:18) was introduced in the coding sequence in order to improve transposase expression. See A. Fire, S. W. Harrison, D. Dixon, *Gene* 93, 189 (1990). (B) Localization of Mos1 insertions into unc-49 and gpa-2 genes after induction of Mos transposase expression in somatic cells. Open triangles: insertion sites; black rectangles: coding exons; white rectangle: non coding exonic sequence. Arrows: genomic primers used to amplify the insertions. (C) Sequence comparison of 22 insertion sites. Insertion sites are oriented relative to the 5' end of the Mos1 transposon. Sequences that flank Mos1 at the right end were identified by PCR. DNA purification and PCR were performed as described in H. G. van Luenen, S. D. Colloms, R. H. Plasterk, *Embo J.* 12, 2513 (1993). The primers in Mos1 were oJL88 (5'-CGCATGCGGCTTACTCAC (SEQ ID NO: 4)) first PCR; and oJL89 (5'-GGCCCCATCCGATTAC-CACCTA (SEQ ID NO: 5)) second PCR. Primers in unc-49 were oJL19 (5'-GCGAAACGCATACCAACTGTA (SEQ ID NO: 6)) first PCR; and oJL20 (5'-TTCATGC-CGAAAAGCAGGCGT (SEQ ID NO: 7)) second PCR. Primers in gpa-2 were the same as described in H. G. van Luenen, S. D. Colloms, R. H. Plasterk, *Embo J.* 12, 2513 (1993). PCR products were gel-purified and sequenced using oJL89 (SEQ ID NO: 5) as a primer. (positive positions on the graph), sequences that flank the left end of Mos1 were deduced from unc-49 and gpa-2 sequences (negative positions on the graph).

FIG. 6 depicts germline mobilization of Mos1. (A) Mos transposase was expressed from an extrachromosomal array using either a glh-2 or a heat-shock promoter. The Mos1 transposon was contained in an array integrated on chromosome V (oxIs25[Mos1;rol-6(sd)]). The array-containing chromosome was balanced by the dpy-11(e224) mutation. In the next generation, catastrophic excision of the transgene was observed (indicated as ΔoxIs) among the progeny. (B) Comparison of excision and insertion frequencies using glh-2 and heat-shock (hsp) promoters to drive Mos transposase expression in the germline. New Mos1 insertions were identified by PCR. Specifically, the presence of Mos1 was detected through PCR by using two primers located in the transposon, oJL102 (SEQ ID NO: 1) and oJL103 (SEQ ID NO: 3). The absence of *D. mauritiana*-flanking sequence was checked using oJL102 (SEQ ID NO: 1) and oJL104 (SEQ ID NO: 2) as described below. In addition, a PCR positive control was performed on each DNA sample using oligonucleotides located in the cha-1 gene. Recombination events were recognized as Dpy worms also containing Mos1 flanked by original *Drosophila* genomic sequences.

FIG. 7 shows Mos1 genomic insertions. (A) Southern blot probed with labeled Mos1 DNA. Lanes 1 to 8, strains in which insertions were detected by PCR; insertions derived from an extrachromosomal array and *Mos* transposase expressed under the heat-shock promoter. Mos1 presence was assessed by PCR using two primers located in the transposon (oJL102 (SEQ ID NO: 1) and oJL103 (SEQ ID NO: 3)). The absence of *D. mauritiana*-flanking sequence was checked using oJL102 (SEQ ID NO: 1) and oJL104 (SEQ ID NO: 2), while a PCR positive control was performed on each DNA sample using oligonucleotides located in the cha-1 gene. The control lane is lin-15(n765) which had been used to build transgenic lines. Each lane contains 2 mg of Bgl II-digested genomic DNA. The Mos1 probe (encompassing bases 1 to 173 of the transposon) was synthesized by PCR using the pBluescriptM13+/*Mos*1 plasmid as a template. (B) Distribution of Mos1 inserts on the physical map of the *C. elegans* genome. Black triangles: insertions from an extrachromosomal array. Open triangles: insertions from the integrated array oxIs25. Open circle: position of oxIs25, the integrated array of Mos1 transposons. (C) DNA sequence of Mos1 de novo insertions oxTi1 through oxTi6, oxTi8, oxTi9, and oxTi11 (SEQ ID NOS:29–46). Genomic fragments that flank the transposon left end were isolated by inverse PCR and sequenced. A primer was designed in the genomic region to the right of the insert and used with a Mos1-specific primer to amplify and sequence the right end flanking the fragment. At insertion sites TA dinucleotides (bold) were duplicated during the process of transposon integration. Lower case: Mos1 sequence. Upper case: genomic sequence. Ellipses: omitted sequence.

FIG. 8 shows a knock-in strategy wherein *Mos*1 excision causes a DNA double strand break, after which a transgene containing sequences homologous to the excision region pairs with the chromosome. Finally, the mutation contained in the transgene is copied into the chromosome.

These drawings only provide information concerning typical embodiments of the invention and are not, therefore, to be considered limiting of its scope.

5. DETAILED DESCRIPTION OF THE INVENTION

The present invention relates to novel methods for generating and identifying mutations in *C. elegans*, and includes methods for introducing a transgene into the *C. elegans* germline. The present invention also includes methods for expressing transgenes in the *C. elegans* germline. The present invention also includes a transgene construct for expression in *C. elegans* and methods for generating mutations by regulating the transposition of endogenous or heterologous transposons in *C. elegans*. The present invention also includes methods for inserting single copy DNA into a *C. elegans* genome by introducing a transgene comprising FLP Recombination Target (FRT) sites into a *C. elegans* genome and causing recombination. FLP is a site-specific recombinase which efficiently catalyzes recombination between FRT sites that have been placed in the genome. K. G. Golic, S. L. Lindquist, *Cell* 44, 521 (1986). When FRT sites are in the same relative orientation within a chromosome, the FLP recombinase excises the intervening DNA from the chromosome. See Golic, Kent G., Generating Mosaics By Site-Specific Recombination, *In Cellular Interactions In Development: A Practical Approach*, 1–31 (D. A. Hartley, ed., Oxford Univ. Press 1993); and Plasterk R. H., Groenen J. T., Targeted Alterations of the *Caenorhabditis elegans* Genome by Transgene Instructed DNA Double Strand Break Repair Following Tc1 Excision, *EMBO J.*, 11:287–90 (1992). Other recombination systems, such as CRE/LOX, could also be used.

All publications, patents, and patent applications cited herein are hereby incorporated by reference. U.S. Patent Application Ser. No. 60/136,972 is hereby incorporated by reference in its entirety.

Definitions

The term "heterologous" is used herein to include nucleic acid sequences such as coding sequences and control sequences that are not normally joined together, and/or are not normally associated with a particular cell. Thus, a heterologous region of a construct or vector is a segment of nucleic acid within or attached to another nucleic acid molecule that is not found in association with this other molecule in nature. For example, a heterologous region of a nucleic acid construct could include a coding sequence flanked by sequences not found in association with the coding sequence in nature (e.g., synthetic sequences having codons different from the native gene). Similarly, a cell transformed with a construct which is not normally present in the cell would be considered heterologous for purposes of this invention. The term includes, but is not limited to, a DNA sequence from another organism.

The term "transgene" is a heterologous sequence that is introduced into an organism. The term includes both sequences that integrate into one or more chromosomal locations of the organism and sequences that are maintained extrachromosomally, e.g., as episomes.

The term "regulable expression control element" includes promoters, polyadenylation signals, transcription termination sequences, upstream regulatory domains, origins of replication, internal ribosome entry sites, enhancers, and the like, which provide for the replication, transcription, and translation of a coding sequence in a recipient cell or in a cell of an organism. The term promoter refers to a DNA sequence that is capable of binding RNA polymerase and initiating transcription of a downstream (3' direction) sequence. Inducible promoters are promoters which are regulable. Such promoters may be regulated by, for example, temperature, small molecules, or developmental stages of an organism.

Inducible promoters include heat-shock promoters, which are induced by exposure to heat. Inducible promoters also include small molecule-regulated promoters. Other inducible promoters include promoters that are induced (or repressed) by tetracycline and its derivatives (Gossen & Bujard, *Proc. Natl. Acad. Sci. USA* 89:5547–5551 (1992)).

"Operably linked" refers to an arrangement of elements in which the components so described are configured so as to perform their usual function. Thus, control sequences such as regulable expression control elements operably linked to a coding sequence are capable of affecting the expression of the coding sequence. The control sequences need not be contiguous with the coding sequence so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3'," or "5'," relative to another sequence, it is to be understood that it is the position of the sequences in the "sense" or "coding" strand of a DNA molecule that is being referred to as conventional in the art.

General Methods

In one embodiment, a method of regulated expression of a heterologous gene in cells of the germline of *C. elegans* comprises the steps of inserting a transgene construct into the *C. elegans*, wherein the construct comprises the heterologous gene operably linked to a promoter, and a 3' untranslated region of a gene that is expressed in the *C. elegans* germline and expressing the heterologous gene. Other embodiments further comprise the use of a promoter which is inducible, such as a heat-shock promoter or a tetracycline-regulated promoter. Yet other preferred embodiments comprise the removal of substantially all bacterial plasmid sequences and repeated sequences from the transgene. In certain other especially preferred embodiments, the method of the present invention comprises the addition of the 3' untranslated region (UTR) of the glh-2 gene, which is expressed in the *C. elegans* germline, to the 3' end of the transgene. A promoter, such as a glh-2 promoter, which is a germline-specific promoter, may be used to drive expression of the transgene.

The present invention further comprises transgene constructs for expression in *C. elegans* which comprises a heterologous gene operably linked to a promoter and a 3' untranslated region of a gene that is expressed in the *C. elegans* germline. In certain embodiments, the promoter is active in the cells of the germline of *C. elegans*. In other embodiments, the promoter comprises an inducible promoter such as a heat-shock promoter or a tetracycline-regulated promoter expressed in the germline. Yet other embodiments comprise the removal of substantially all bacterial plasmid sequences and repeated sequences from the transgene. In certain preferred embodiments, the method of the present invention comprises the addition of a 3' untranslated region (UTR) of a glh-2 gene, which is expressed in the *C. elegans* germline, to the 3' end of the transgene. A promoter, such as a glh-2 promoter, may be used to drive expression of the transgene. In still other embodiments, the heterologous gene codes for a transposase. In certain preferred embodiments, the heterologous gene is a TC3A transposase gene.

The present invention also includes methods for generating mutations in the genome of *C. elegans* by using controlled mobilization of transposons. In certain embodiments, the method for generating mutations in the genome of *C. elegans* comprises the steps of introducing a transgene construct comprising a transposase gene which is operably linked to a regulable expression control element and a 3' untranslated region of a gene that is expressed in the *C. elegans* germline into *C. elegans* and expressing the transposase gene. Such methods allow the generation of mutants in which the mutated genes are tagged by the insertion of the transposon. PCR-based techniques permit fast identification of the transposon insertion that causes the mutation. Since the *C. elegans* genome has been entirely sequenced, sequencing of the genomic regions that flank the transposon allows immediate identification of the mutated gene.

In certain embodiments, transposons used in the method of the present invention are endogenous transposons. Several different types of endogenous transposons are present in *C. elegans*, and these can be mobilized in mutator strains. See, e.g., R. H. A. Plasterk, H. G. A. M. van Luenen, in *C. elegans II*, D. L. Riddle, T. Blumenthal, B. J. Meyer, J. R. Priess, Eds. (Cold Spring Harbor Laboratory Press, New York, 1997) pp. 97–116. Mutator alleles have been useful in cloning *C. elegans* genes, particularly in early studies before the genome project reagents were widely available. In certain preferred embodiments, the endogenous transposons are Tc3 transposons. In yet other embodiments, the transposase gene is a TC3A transposase gene. In still other embodiments, the regulable expression control element is an inducible promoter, comprising in some embodiments a heat-shock promoter or a tetracycline-regulated promoter. Yet other embodiments comprise the removal of substantially all bacterial plasmid sequences and repeated sequences from the transgene construct. In certain preferred embodiments, the method of the present invention comprises the addition of the 3' untranslated region (UTR) of the glh-2 gene, which is expressed in the *C. elegans* germline, to the 3' end of the transgene. In such embodiments, the regulable expression control element comprises a promoter, such as a glh-2 promoter or a heat-shock promoter, which may be used to drive expression of the transgene.

In other embodiments, mutants may be generated by using controlled mobilization of heterologous transposons. Using a heterologous transposon allows researchers to tag mutated genes with a sequence that is unique in *C. elegans* genome. These tagged mutations will allow the rapid cloning of the mutated genes. The primary advantage over the endogenous transposon scheme is that this method avoids the isolation of irrelevant insertions of the endogenous *C. elegans* transposons. A further advantage is that the expression of the heterologous transposase would only mobilize the heterologous element, and thus mutations should only be due to insertions of these elements. Additionally, insertions could be stabilized by loss of the transposase-expressing construct.

In certain preferred embodiments, Mos1, a mariner-like transposon isolated from *Drosophila mauritiana*, is used M. Medhora et al., *Genetics* 128:311–318 (1991). See generally D. L. Hartl et al., *Annu. Rev. Genet.* 31:337–358 (1997). Mos1 is a member of the mariner/Tc1 family and was initially identified in the fruitfly *Drosophila mauritiana*. J. W. Jacobson, M. M. Medhora, D. L. Hartl, *Proc. Natl. Acad. Sci. USA* 83, 8684 (1986). Like the other members of the mariner/Tc1 family, Mos1 contains a single open reading frame which encodes the transposase. The transposase binds to and cleaves at the inverted terminal repeats (ITRs) present at each end of the transposon. See, e.g. D. L. Hartl, A. R. Lohe, E. R. Lozovskaya, *Annu. Rev. Genet.* 31, 337 (1997); R. H. Plasterk, Z. Izsvak, Z. Ivics, *Trends Genet.* 15, 326–332 (1999). The Mos1 transposase is the only protein necessary for transposition in vitro. L. R. Tosi, S. M. Beverly, *Nucleic Acids Res.* 28, 784 (2000). Because no additional factors are required for transposition, the Mos1 transposon should be capable of transposition in heterologous species, and indeed the transposon has been mobilized in species evolutionarily distant from *Drosophila*. F. J. Gueiros-Filho, S. M. Beverly, *Science* 276, 1716 (1997); J. M. Fadool, D. L. Hartl, J. E. Dowling, *Proc. Natl. Acad. Sci. USA* 95, 5182 (1998); A Sherman, et al., *Nat. Biotechnol.* 16, 1050 (1998); C. J. Coates, N. Jasinskeine, L. Miyashiro, A. A. James, *Proc. Natl. Acad. Sci. USA* 95, 3748 (1998).

In other embodiments, the transposase gene comprises restriction sites 5' of the start codon, restriction sites 5' of the stop codon, and an artificial intron in the transposase gene open reading frame. Other preferred embodiments involve a regulable expression control element which comprises an inducible promoter such as a heat-shock promoter or a tetracycline-regulated promoter. Yet other preferred embodiments comprise the removal of substantially all bacterial plasmid DNA sequences and repeated sequences from the transgene construct. In certain preferred embodiments, the method of the present invention comprises the addition of the 3' untranslated region (UTR) of the glh-2 gene, which is expressed in the *C. elegans* germline, to the 3' end of the transgene. In such embodiments, the regulable expression control element may comprise a promoter, such as a glh-2 promoter, a myo-3 promoter or a heat-shock promoter, which may be used to drive expression of the transgene.

In yet other embodiments, the method of the present invention includes engineering the transposon to carry a heterologous DNA sequence into a *C. elegans* chromosome. Certain embodiments of the method of the current invention may comprise the steps of introducing a transposon into the *C. elegans*, wherein the transposon comprises the heterologous DNA sequence; introducing a transgene construct into the *C. elegans*, wherein the construct comprises a transposase gene which is operably linked to a promoter and a 3' untranslated region of a gene that is expressed in the *C. elegans* germline; and expressing the transposase, such that the transposon integrates as a single copy into a *C. elegans* chromosome.

In some embodiments, the transposon may be modified to contain bacterial plasmid DNA sequences. Such sequences may simplify cloning of mutated genes into bacteria from *C. elegans* genomic DNA preparations. In yet other embodiments, the transposon may carry a gene useful for selection or screening purposes.

In certain preferred embodiments, FRT/FLP or CRE/LOX recombination sites could be inserted into the transposon. One of skill in the art would appreciate that an engineered transposon carrying such recombination sites would facilitate insertion of single copy DNA into the *C. elegans* genome. In other embodiments, the transposon could include polyadenylation sites or transcriptional terminators.

In yet other preferred embodiments, the promoter is inducible. In such embodiments, inducible promoters such as a heat-shock promoter, may be used. Yet other preferred embodiments comprise the removal of substantially all bacterial plasmid DNA sequences and repeated sequences from the transgene construct. In certain preferred embodiments, the method of the present invention comprises the addition of the 3' untranslated region (UTR) of the glh-2 gene, which is expressed in the *C. elegans* germline, to the 3' end of the transgene. In such embodiments, the regulable expression control element may comprise a promoter, such as a glh-2 promoter, a myo-3 promoter or a heat-shock promoter, which may be used to drive expression of the transgene.

6. EXAMPLES

The following examples are given to illustrate several embodiments which have been made within the scope of the present invention. It is to be understood that these examples are neither comprehensive nor exhaustive of the many types of embodiments which can be prepared in accordance with the present invention.

Example I

Mobilization of Endogenous Tc3 Transposons

About 15 copies of the Tc3 transposon are present in the genome of the wild-type *C. elegans* N2 strain. These transposable elements are inactive in wild-type animals. Our goal is to cause specific mobilization of the endogenous Tc3 copies by expressing the TC3A transposase in the germline. New Tc3 insertions will be used as tags to clone the genes which they have disrupted.

1—TC3A Expressed Under the ced-9 Promoter Causes Somatic and Germline Hops:

The TC3A transposase gene has been cloned behind a ced-9 promoter. This construct has been coinjected with linearized *C. elegans* genomic DNA and the lin-15(+) plasmid into a lin-15(−) strain and unstable transgenic strains have been obtained. Transposase activity was assayed by testing whether the construct could excise a Tc3 element from the unc-22 gene and restore the function of the locus. The ced-9::Tc3A arrays have been crossed into unc-22 (r750::Tc3); lin-15(n765ts) background. Wild-type revertants have been recovered from Unc-22 F1 animals, suggesting functional expression of the TC3A transposase. One of these extrachromosomal arrays was integrated into a chromosomal location to generate the insertion oxIs17[ced-9::Tc3A; lin-15(+)].

oxIs17 was mapped on the X chromosome and functionally characterized. lin-15(n765ts); oxIs17[ced-9::Tc3A; lin-15(+)] males were crossed to unc-22(n750::Tc3); lin-15 (n765ts) hermaphrodites. Heterozygous nonUnc nonLin hermaphrodites were cloned and allowed to self-fertilize. It was expected that among the progeny of these animals, there would be found ¼ Unc animals homozygous for unc-22 (r750::Tc3). Of those Unc individuals, ¾ should be either homozygous or heterozygous for oxIs17 i.e. nonLin. It was observed, however, that the Unc nonLin animals were greatly under-represented; instead, there were many more nonUnc individuals. Since the ced-9 gene is ubiquitously expressed, it was reasoned that TC3A could be present not only in the germline but also in somatic cells and could cause somatic reversion of the Unc phenotype. To test this hypothesis, nonUnc nonLin individuals were cloned, assuming that a fraction of them could be homozygous for unc-22(r750::Tc3) despite their wild-type phenotype. Self-progeny of these animals were scored. Individuals heterozygous for oxIs17 segregated ¼ Lin animals (which no longer expressed the TC3A transposase). In this category, plates were identified in which 100% of the Lin worms were Unc while almost 100% of the nonLin were nonUnc. Hence, the parent hermaphrodite must have been homozygous unc-22 (r750::Tc3) mutant although its phenotype was wild-type. These data demonstrate that ced-9::Tc3A causes somatic reversion of the unc-22(r750::Tc3) locus at high frequency.

Rare nonUnc Lin were looked for among the Lin animals generated by self-fertilization of unc-22(r750::Tc3); lin-15 (−); oxIs17/+ hermaphrodites to determine germline reversion rates. Since the Lin worms had lost oxIs17 and had no TC3A transposase expressed somatically during development, the only way to revert the Unc phenotype was to receive one reverted copy of the unc-22 locus. This reversion event had to occur during germline development. Rare nonUnc Lin progeny were identified among Unc Lin progeny (experiment #1: 1 nonUnc Lin in 61 Lin total; exp. #2: 2/106; exp. #3: 4/203). It was concluded that ced-9::Tc3A causes an approximately 2% reversion rate of the unc-22 (r750::Tc3) locus in the germline.

2—Expression of TC3a Using a glh-2 Promoter:

Since the somatic reversion caused by ced-9::Tc3A causes a discrepancy between the phenotype and the genotype of an individual carrying a locus disrupted by a Tc3 insertion, a TC3A expression vector was designed based on the germline-specific glh-2 gene (gift of Karen Bennett). A plasmid containing a glh-2 genomic fragment is able to rescue the Glh-2 mutant phenotype and is therefore likely to be expressed in the germline. The glh-2 open reading frame was deleted and replaced by a multiple cloning site to generate an expression cassette that retains glh-2 promoter and 3' untranslated regions. Tc3A was inserted to generate glh-2::Tc3A. This construct has been coinjected with linearized C. elegans genomic DNA and the lin-15(+) plasmid into a lin-15(−) strain and several unstable transgenic strains have been obtained. A plasmid driving strong expression of the Green Fluorescent Protein (hereinafter "GFP") in the coelomocytes (gift of Piali Sengupta) has also been incorporated in this array. This allows monitoring of the presence of the array in a lin-15(+) background based on GFP expression.

As described above, these arrays have been crossed into unc-22(r750::Tc3); lin-15(n765ts) background. In contrast to the ced-9::Tc3A experiments, no somatic reversion events were observed. Germline reversion events were observed in the progeny of unc-22; oxEx[glh-2::Tc3A] hermaphrodites (experiment #1: 2/1914 total scored animals; experiment #2: 5/4312). It was concluded that glh-2::Tc3A causes a 0.1% reversion rate of the unc-22(r750::Tc3) locus in the germline.

Example 2

Expression of the Mariner Transposase in *C. elegans*

A mutagenesis strategy was also developed that uses the mariner transposon from the hornfly (gift of David Lampe and Hugh Robertson). Mariner transposons from *Drosophila* are related to *C. elegans* Tc transposons. In fact, members of the Tc/mariner family of transposable elements have been identified in a broad range of species. R. H. A. Plasterk & H. G. A. M. van Luenen, Transposons, in *C. elegans II* 97–116 (D. L. Riddle et al. eds., 1997). Horizontal transfer may be responsible for the broad distribution of this family of transposable elements. Horizontal transfer implies that specific host factors are not required for transposition and biochemical characterization has borne this supposition out. Purified transposase is able to catalyze the transposition of mariner or of Tc elements from a host plasmid to a target plasmid. D. J. Lampe et al., *EMBO J.* 15:5470–5479 (1996); J. C. Vos et al., *Genes Dev.* 10:755–761 (1996). This has enabled researchers to mobilize mariner elements from *Drosophila* in other Dipteran species. T. G. Loukeris et al., *Proc. Natl. Acad. Sci. USA* 92:9485–9489 (1995); T. G. Loukeris et al., *Science* 270:2002–2005 (1995); A. R. Lohe & D. L. Hartl, *Genetics* 143:365–374 (1996). Recently, a mariner element from *Drosophila* has been mobilized in *Leishmania*, which represents a trans-kingdom transposition. F. J. Gueiros-Filho & S. M. Beverly, *Science* 276: 1716–1719 (1997). Thus, it was possible that mariner would be active in *C. elegans* as well.

A plasmid encoding the mariner transposase HIMAR1 was received from David Lampe and Hugh Robertson. First, the transposase coding sequence was engineered to allow for efficient expression in *C. elegans*. Restriction sites were inserted immediately upstream to the start codon and just before the stop codon to facilitate subcloning of the fragment in various expression vectors. An artificial intron was inserted in the open reading frame since the presence of introns improves the expression level of transgenes in *C. elegans*.

Engineered Himar1 was placed under the control of the muscle-specific promoter myo-3. The myo-3::Himar1 construct was injected with the lin-15(+) plasmid into a lin-15 (−) strain and unstable transgenic strains obtained. Expression of the HIMAR1 transposase was examined first by Western Blot. Extracts were prepared from oxEx[myo-3:: Himar1; lin-15(+)] worms, run on a denaturing acrylamide gel and transferred to a nitrocellulose membrane. The membrane was probed with previously characterized antibodies that recognize the HIMAR1 protein (provided by David Lampe and Hugh Robertson). In extracts of transgenic worms, an approximately 42 kD protein which corresponds to the expected molecular weight of HIMAR1 was detected. The signal was absent from non-transgenic worm extracts. Using the same antibodies, the protein was visualized in situ using immunofluorescence on oxEx[myo-3::Himar1; lin-15 (+)] worms. Intense immunoreactivity was detected which was restricted to the nuclei of muscle cells. These data indicate that the HIMAR1 mariner transposase is expressed and properly targeted to nuclei in *C. elegans* cells.

Example 3

Germline Expression of the Transposase Using the glh-2 Promoter

Generation of heritable Mos1 insertions would require expression of the Mos transposase in the germline. However, expression of transgenes in the germline of *C. elegans* is not possible using standard techniques. Typically, transgenic worms are generated by injecting plasmid DNA into the gonads of *C. elegans* (C. C. Mello, J. M. Kramer, D. Stinchcomb, V. Ambros, *Embo J* 10, 3959 (1991)). These fragments then form a simple array of repeated DNA segments. Although gene expression is robust in somatic tissues, such simple arrays are not expressed in the germline or are silenced after a few generations. Co-injection of genomic DNA with plasmid DNA improves germline expression, presumably by preventing tandem repeats in the array. W. G. Kelly, S. Xu, M. K. Montgomery, A. Fire, *Genetics* 146, 227 (1997). To express the Mos transposase in the germline, an expression vector containing the promoter and the 3' UTR of the glh-2 gene was built. This gene encodes a germline helicase which is specifically expressed in the gonad. M. E. Gruidl, et al., *Proc. Natl. Acad. Sci. USA* 93, 13837 (1996). Transgenic lines carrying extrachromosomal arrays of the glh-2::Mos transposase construct were generated by microinjection. To maximize expression in the germline, constructs were isolated from plasmid vector sequences and were coinjected with fragmented genomic DNA. (The Mos transposase coding sequence was introduced between the promoter and the 3' UTR of glh-2. Specifically, this construct (pJL9) contains 2.2 kb of the glh-2 genomic sequence immediately upstream of the translation start site (nt 29,882 to 32,095 in cosmid C55B7), an Mlu I-Nhe I cloning site, and 0.8 kb of sequence immediately downstream of the glh-2 stop codon. An Mlu I-Nhe I fragment containing the Mos transposase was subcloned into pJL9 to generate the glh-2::MosTransposase construct. lin-15(n765) hermaphrodites were injected with a Spe I-Kpn I fragment of glh-2::MosTransposase (injection concentration 10 ng/µl), with lin-15(+) (EKL15) and ofm-1::gfp (pPD97/98) fragments and N2 worm genomic DNA as described above for the generation of the oxEx166[hsp::MosTransposase] array.

Transposase expression in the germline was determined by assaying for excision of transposons from a defined chromosomal location. Specifically, the Mos1-containing extrachromosomal array was integrated into chromosome V to generate oxIs25[Mos1;rol-6(sd)]. The oxIs25 array was mapped less than 0.54 map units from dpy-11. Heterozygous oxIs12/dpy-11 worms were generated. These animals largely segregated Dpy and Rol progeny as expected for these closely linked markers (FIG. 6). However, when the glh-2::Mos Transposase transgene was crossed in, approximately 16% of the nonDpy progeny were nonRol (15.7%±0.9, mean±SEM, n=44 plates). The nonRol phenotype was stably inherited. It was hypothesized that in those worms, the Mos transposase excised Mos1 from the integrated array. The resulting DNA breaks were responsible for catastrophic excision of the entire locus, including interspersed rol-6 copies. The correlated loss of rol-6(sd) and Mos1 was confirmed by PCR, in which NonRol individuals were cloned, selfed and DNA was purified from the progeny. Mos1-containing fragments were detected by PCR using one primer complementary to Mos1 (oJL102: 5'-CAACCT-TGACTGTCGAACCACCATAG (SEQ ID NO: 1)) and one primer complementary to D. mauritiana-flanking DNA (oJL104:5'-ACAAAGAGCGAACGCAGACGAGT (SEQ ID NO: 2)). Of 188 nonRol worms, only one individual retained a copy of the Mos1 fragment that was initially present in the transgene. Based on the phenotypic reversion of the Rol phenotype, it was calculated that 1 in 5 chromosomes experienced catastrophic excision of the transgene (20.9%±1.1%, mean±SEM, n=44 plates). The probability p of a single chromosome containing the array of Mos1 elements transgene experiencing "catastrophic excision" can be derived from a Punnett square where the ratio R of nonRol worms over the total number of the progeny: $R=1/4p+1/4p+(1/2p)_2$. These results demonstrated that the glh-2-based expression vector expressed the transposase in the germline and that the Mos1 transposon in the chromosome was recognized as a substrate.

To determine if excision of Mos1 from the array was associated with insertion in the genome, the progeny of animals expressing the transposase in the germline were screened for de novo insertions. Specifically, using PCR, the presence of the Mos1 element in the absence of the Drosophila sequences which flank the transposon in the array was assayed. Mos1 presence was assessed by PCR using two primers located in the transposon (oJL102 (SEQ ID NO: 1) and oJL103:5'-TCTGCGAGTTGTTTTTGCGTTTGAG (SEQ ID NO: 3)). The absence of D. mauritiana-flanking sequence was checked using oJL102 (SEQ ID NO: 1) and oJL104 (SEQ ID NO: 2) as described above. In addition, a PCR positive control was performed on each DNA sample using oligonucleotides located in the cha-1 gene. Because the integrated array containing unmobilized transposons also contained rol-6(sd), insertions were sought in nonRol progeny; specifically, either nonRol animals that experienced catastrophic excision of the array or Dpy progeny (FIG. 6B) were analyzed. Insertions were identified in 1% of nonRol progeny (2/227) and in 10% of Dpy progeny (11/116 F1+F2 Dpys). These results demonstrated that transposition of Mos1 could be achieved in the C. elegans germline. However, it was observed that high rates of excision were not accompanied by high rates of insertion; these results support previous data indicating that these two processes are not coupled. H. G. van Luenen, S. D. Colloms, R. H. Plasterk, Cell 79, 293 (1994).

Using integrated arrays as a source of transposons prevents the easy recovery of new insertions that occur on the same chromosome; this bias could be circumvented by using an extrachromosomal array of transposons. In addition, extrachromosomal arrays are not completely stable in meiosis, which makes the isolation of strains lacking unmobilized transposons easy after mobilization. Therefore, it was tested whether Mos1 could be mobilized from an extrachromosomal array into the chromosomes. Specifically, the glh-2::Mos Transposase construct was used to mobilize transposons from a Mos 1-bearing array (oxEx164[Mos1; rol-6(sd)]). The nonRol progeny from double transgenic animals (oxEx167[glh-2::MosTransposase]; oxEx164[Mos1; rol-6(sd)]) were analyzed for transposition events using PCR. An insertion frequency of 1% (3 insertions/302 progeny, Table 1) was detected. Thus, these results closely match those obtained for integrated arrays.

Table 1. Frequencies of Mos1 genomic insertions from an extrachromosomal array. nonRol progeny of oxEx164 [Mos1; rol-6(sd)]; oxEx[MosTransposase] were analyzed by PCR for the presence of Mos1 and the loss of the Drosophila-flanking sequences present in the donor plasmid. Mos1 presence was assessed by PCR using two primers located in the transposon (oJL102 (SEQ ID NO: 1) and oJL103:5'-TCTGCGAGTTGTTTTTGCGTTTGAG (SEQ ID NO: 3)). The absence of D. mauritiana-flanking sequence was checked using oJL102 (SEQ ID NO: 1) and oJL104 (SEQ ID NO: 2) as described above. In addition, a PCR positive control was performed on each DNA sample using oligonucleotides located in the cha-1 gene. When heat-shocked (1 hour at 35° C.) P0s were moved to fresh plates and eggs were collected for the next 24 hours. *During experiment #5 the stability of the oxEx164[Mos1; rol-6(sd)] transgene reached 75% while in previous experiments, it was approximately 20%.

|  | Transposition frequency | | | |
| --- | --- | --- | --- | --- |
| Transposase construct | no heat-shock | | with heat shock | |
| glh-2::MosTransposase | exp #1: 2/108 | 1.9% | exp #1: ND | |
|  | exp #2: 0/104 | 0% | exp #2: ND | |
|  | exp #3: 1/90 | 1.1% | exp #3: 0/65 | 0% |
| hsp::MosTransposase | exp #1: ND | | exp #1: 4/65 | 6.2% |
|  | exp #2: 0/33 | | exp #2: 3/98 | 3.1% |
|  | exp #3: 0/39 | | exp #3: 6/87 | 6.8% |
|  | exp #4: ND | | exp #4: 5/85 | 5.9% |
|  | exp #5: 0/44* | | exp #5: 15/34* | 44.1% |

Example 4

Mos1-Mobilization in the Germline Using a Heat-Shock Promoter

The glh-2 promoter expresses the transposase in the germline constitutively. Constitutive expression of the transposase has two disadvantages. First, crosses must be set up fresh every generation to guarantee that the array remains intact and does not accumulate inherited changes. Second, because the tranposase was expressed in the germline early in development, events identified in the progeny might not be independent but might have occurred when the germline was still comprised of only few cells. Expression limited to adults can be achieved by using a heat-shock promoter. Expression of the transposase could be induced after a strain containing the transposase and transposons had been propagated and expanded to many animals. In addition, heat-shocking animals with mature germlines would maximize the independence of insertion events. Animals expressing the transposase under the control of the heat-shock promoter and bearing the integrated transposon (oxIs25/dpy-11; oxEx166[hsp::Mos Transposase]) were heat-shocked. P0s could only be heat-shocked for 45 minutes; such animals were almost paralyzed, stopped eating and had low brood sizes. Longer heat-shock caused the animals to die. It was speculated that this lethality is due to high rates of transposition in somatic cells. Ubiquitous expression of the transposase would cause double strand breaks in the chromosome at the site of integration in every cell which may cause cell cycle arrest or apoptosis. G. Evan, T. Littlewood, *Science* 281, 1317 (1998).

F1 progeny were analyzed for catastrophic excision, that is, for the appearance of nonRol nonDpy progeny (FIG. 6A). In contrast with results obtained using the glh-2 expression vector, catastrophic excision was not observed. Only rare nonRol progeny were generated which were likely to be the result of recombination between the array and the dpy marker (FIG. 6B). However, by analyzing the Dpy progeny of heat-shocked animals, it was discovered that the heat-shock construct caused the efficient insertion of Mos into new locations in the genome. Approximately 27% (25/94) of F1 or F2 Dpy worms carried novel transposon insertions (FIG. 6B). In addition to novel insertions, recombinant chromosomes containing both the dpy marker and the original array arose at high frequency. These were identified as Dpy animals containing transposons flanked by *Drosophila* DNA. This hotspot for recombination is likely to arise as a result of double strand breaks introduced into the array by the transposase. A. R. Lohe, C. Timmons, I. Beerman, E. R. Lozovskaya, D. L. Hartl, *Genetics* 154, 647 (2000).

It was then tested whether transposition could occur from an extrachromosomal array using the heat-shock promoter construct to express the transposase (oxEx166; oxEx164 [Mos1; rol-6(sd)]). Hermaphrodites bearing both arrays were heat-shocked as young adults. The nonRol progeny were analyzed by PCR for transposition events. New insertions were observed in 8.9% of the F1 (33/369 progeny, Table 1). Since transposition could have occurred into the transposase-containing array, F2 animals that lost this array were isolated from eight transposon-bearing strains. Genomic DNA was prepared from these strains and analyzed for the presence of Mos1. The transposon was still detected in all eight strains, thus demonstrating that the transposon had not inserted in the array. No insertions could be detected in 116 F1 clones derived from non-heat-shocked parents. The frequency of transposition was low but one of the main limiting factors is the stability of the extrachromosomal array that is used as a transposon source. The initial experiments were performed when the array was only 20% stable and transposition frequencies were in the range of 5%; when the array matured and was about 75% stable, transposition frequency reached 44%. Generating more stable extrachromosomal arrays could increase the frequencies of transposition.

The heat-shock promoter was able to drive expression of Mos transposase in the germline and to promote transposition events at a higher rate than obtained using the glh-2 construct. Temperature has been shown to affect transposition frequency in other organisms. D. Garza, M. Medhora, A. Koga, D. L. Hartl, *Genetics* 128, 303 (1991). One possible explanation for the efficient transposition observed after heat-shock is that chromatin structure is somehow altered by the heat-shock. Therefore, it was tested whether heat-shock itself could account for the difference in transposition frequencies. Parents with extrachromosomal arrays carrying the glh-2-transposase construct and carrying the transposon were heat-shocked and progeny were tested for transposition. The frequency of transposition was not improved by the heat-shock treatment (Table 1). Thus, heat-shock itself does not facilitate efficient transposition.

Example 5

Transposition in Somatic Cells

To determine whether the Mos1 element could be mobilized in *C. elegans* cells, Mos1 transposition in somatic cells was first analyzed. The gene encoding the Mos1 transposase was engineered to improve expression in the worm and placed under the control of a heat-shock promoter. The Mos transposase encoding sequence was PCR amplified out of pBluescribe M13+/Mos1 (M. Medhora, K. Maruyama, D. L. Hartl, *Genetics* 128, 311 (1991), modified as described in FIG. 5A and subcloned as a Mlu I-Nhe I fragment between the hsp-16-48 promoter (H. G. van Luenen, S. D. Colloms, R. H. Plasterk, *Embo J*. 12, 2513 (1993)); E. P. Candido, et al., *Genome* 31, 690 (1989) and the glh-2 3' untranslated region (fragment 35383 to 36190 in cosmid C55B7) (M. E. Gruidl, et al., *Proc. Natl. Acad. Sci. USA* 93, 13837 (1996) (FIG. 5A). The resulting construct was used to generate the extrachromosomal array oxEx166[hsp::MosTransposase]. (lin-15(n765) hermaphrodites were injected in the syncitial gonad with a mixture of the following gel-purified fragments: a Hind III-Eco RI fragment of hsp::Mos Transposase (injection concentration: 10 ng/µl), a Pst I-Bsi WI fragment of the ofm-1::gfp construct (pPD97/98) that expresses GFP in the coelomocytes (gift of Piali Sengupta) (injection concentration: 5 ng/µl) and a Kpn I-Eag I fragment of EKL15 (lin-15+) (S. G. Clark, X. Lu, H. R. Horvitz, *Genetics* 137, 987 (1994)) (injection concentration: 10 ng/µl). Plasmid backbones were removed from all purified fragments. Eco RV-digested N2 worm genomic DNA was coinjected at a concentration of 70 ng/µl. Another extrachromosomal array, oxEx164[Mos1; rol-6(sd)], contained the Mos1 transposon. (lin-15(n765) hermaphrodites were injected with a 2.2 kb Xho I-Hind III fragment of pBluescribe M13+/Mos1 that contains the 1.3 kb Mos1 element flanked by *D. simulans* sequences (M. Medhora, K. Maruyama, D. L. Hartl, *Genetics* 128, 311 (1991) (injection concentration: 10 ng/µl) and a 2.2 kb rol-6(sd) fragment of pRF4 (J. M. Kramer, R. P. French, E. C. Park, J. J. Johnson, *Mol. Cell. Biol*. 10, 2081 (1990) (injection concentration: 10 ng/µl). Eco RV-digested N2 worm genomic DNA was coinjected at a concentration of 80 ng/µl to increase the complexity of the array; this array also contained the dominant genetic marker rol-6(sd) which causes animals to roll instead of swimming in a sinusoidal fashion. These two strains were crossed and progeny carrying both arrays were heat-shocked as young adults. After 12 hours, the heat-shocked animals were harvested and genomic DNA was prepared. Mos1 transposition was detected using the strategy developed by van Luenen et al. See H. G. van Luenen, S. D. Colloms, R. H. Plasterk, *Embo J*. 12, 2513 (1993). Specifically, insertions were identified by PCR amplification using one set of primers complementary to the transposon and another set complementary to an arbitrary target gene. DNA purification and PCR were performed as described in H. G. van Luenen, S. D. Colloms, R. H. Plasterk, *Embo J* 12, 2513 (1993). The primers in Mos1 were oJL88 (5'-CGCATGCGGCTTACTCAC (SEQ ID NO: 4)) first PCR; and oJL89 (5'-GGCCCCATCCGAT-TACCACCTA (SEQ ID NO: 5)) second PCR. Primers in unc-49 were oJL19 (5'-GCGAAACGCATACCAACTGTA (SEQ ID NO: 6)) first PCR; and oJL20 (5'-TTCATGC-CGAAAAGCAGGCGT (SEQ ID NO: 7)) second PCR. Primers in gpa-2 were the same as described in H. G. van Luenen, S. D. Colloms, R. H. Plasterk, *Embo J* 12, 2513 (1993). PCR products were gel-purified and sequenced using oJL89 (SEQ ID NO: 5) as a primer. A PCR product can be obtained only if a transposon has integrated into the target gene. The method is sensitive enough to detect a single insertion in the target gene in a single somatic cell of an adult animal. Insertions in two genes were assayed: the gpa-2 gene which encodes a G protein subunit (R. R. Zwaal, J. E. Mendel, P. W. Stemberg, R. H. Plasterk, *Genetics* 145, 715 (1997)), and the unc-49 gene which encodes a GABA receptor. B. A. Bamber, A. A. Beg, R. E. Twyman, E. M. Jorgensen, *J. Neurosci.* 19, 5348 (1999). Mos1 insertions were detected in both genes (2.5±1.0 inserts in 10 ng of genomic DNA, mean±S.D., n=5 experiments). Given that the maximal distance of the inserts from our gene primers was approximately 1 kb, it was estimated that an average of 10 insertions occurred per cell in heat-shocked animals. Insertions were also detected at low frequency in worms that contained the transposon array but lacked the transposase expression construct (0.09 insertions in 10 ng DNA, n=2 experiments). These data indicated that low levels of Mos1 transposase were expressed from the intact Mos1 transposons in the extrachromosomal array.

Figure 5C:
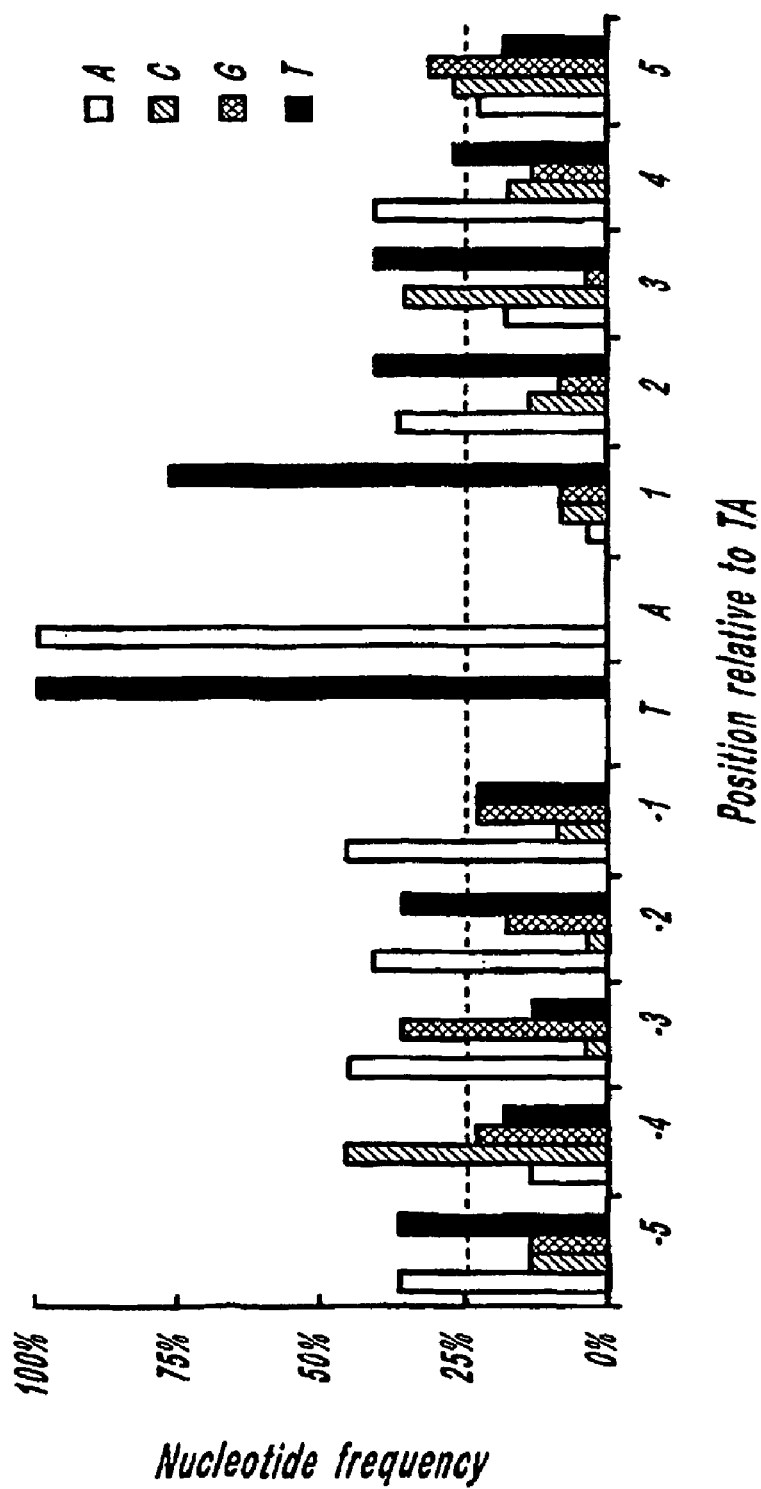

To demonstrate that these transposon insertions represented bona fide transposition events, PCR products were gel-purified and the sequence of the insertion sites from the somatic transposition assays was determined. In all cases, the Mos1 inverted terminal repeats were complete, the *Drosophila* sequences that flanked Mos1 in the donor plasmid were no longer present, and the insertions all took place at a TA dinucleotide. Transposon insertions were distributed uniformly in exons, introns and 3' noncoding sequences of gpa-2 and unc-49 (FIG. 5B). Comparison of 22 insertion sites did not reveal a strong consensus site apart from a bias toward a T at position +1 with respect to the TA dinucleotide (FIG. 5C). These data demonstrated that Mos1 can hop into *C. elegans* chromosomes and that the transposase was sufficient to catalyze insertion without *Drosophila* host factors.

Example 6

Introduction of Mariner Transposon Copies into the *C. elegans* Genome

The full-length copy of the hornfly mariner transposon Autmar was gel-purified to remove non-nematode plasmid sequences. Purified Autmar was injected with linearized *C. elegans* genomic DNA and the rol-6(dm) plasmid into lin-15(n765ts) worms and unstable transgenic strains were recovered. Due to the presence of rol-6(dm) in the array, transgenic animals roll instead of displaying normal sinusoidal locomotory movements. These animals are Lin when grown at the nonpermissive temperature because they are genotypically lin-15(−). This array was integrated into a chromosomal location to generate the oxIs21 insertion. oxIs21 was mapped to chromosome X, 2.5 m.u. away from the lon-2 locus.

Example 7

The Mariner Transposase Can Excise Mariner Transposons from *C. Elegans* Chromosomes in the Germline Engineered Himar1 was inserted in the glh-2 germline expression cassette described above. The glh-2::Himar1 construct was co-injected with linearized *C. elegans* genomic DNA and the lin-15(+) plasmid into lin-15(n 765ts) worms. The oxEx115 extrachromosomal array is transmitted at each generation to a large fraction of the progeny.

lin-15(n765ts); oxEx119[glh-2::Himar1; lin-15(+)] males were crossed into lin-15(n765ts) oxIs21[Autmar; rol-6(sd)] hermaphrodites. As predicted, animals of the cross-progeny were Rol nonLin. At the next generation, it was expected that ⅓ of the Rol animals would be found to be homozygous for oxIs21. However, among 48 Rol nonLin cloned individuals, none segregated more than approximately 75% Rols, while 6 of 15 Rol Lin hermaphrodites segregated 100% Rol progeny. After careful characterization of the progeny of parent animals exhibiting various phenotypes, it was concluded that oxEx115 could elicit the reversion of the Rol phenotype. Presumably, the reversion is caused by excision of the Autmar transposons from the integrated array which in turn leads to loss of the adjacent rol-6(dm) genes by imprecise repair of the locus. It was concluded that the mariner transposase can excise mariner transposons from *C. elegans* chromosomes in the germline.

Example 8

Mobilization of a Heterolog us Mariner Transpos n in the *C. elegans* Genome

Materials and Methods:

Reagents

Mos1-Containing Strain:

The transgenic strain EG1638 that contains Mos1 has been generated by coinjection of lin-15(n765) worms with:
 the 2.2 kB Xho I-Hind III fragment of pBluescribe M 13+/Mos1, M. Medhora et al., *Genetics* 128:311–318 (1991); (injection concentration: 10 ng/µl)
 the 2.2 kB Hind III rol-6 rescuing fragment containing the semi-dominant mutation rol-6(sul O06), J. M. Kramer et al., *Mol. Cell. Biol.* 10:2081–2089 (1990); (injection concentration: 10 ng/µl)
 EcoRV-digested genomic DNA prepared from N2 worms (injection concentration: 80 ng/µl)

The resulting strain lin-15(ts); oxEx164[Mos1; rol-6(sd)] exhibits a Rol Muv phenotype when grown above 20° C. The Muv phenotype is not expressed when worms are grown at 15° C.

Mos 1 transpos-expressing strain:

As shown in FIG. 2, the expression vector pJL44 (HSP::MosTase::glh-2) contains the following elements:
 a 377 bp Hsp16-48 heat-shock promoter fragment recovered by PCR from pRP176, H. G. van Luenen et al., *EMBO J.* 12:2513–2520 (1993), using the oligos oJL21 5'-CGAAGCTTGCTGGACGGAAATAGTGG (SEQ ID NO: 19) and oJL22 5'-CGACGCGTTCT-TGAAGTTTAGAGAAT (SEQ ID NO: 20).

a 1088 bp fragment containing the Mos1 transposase coding sequence amplified by PCR from pBluescribe M 13+/Mos1 using oJL77 5'-GCACGCGTTATGTC-GAGTTTCGTGCCGAATAAAG (SEQ ID NO: 21) and oJL78 5'-GCGCTAGCTATTCAAAGTATTTGC-CGTCGCTCGCGACACATTTTTCCCA (SEQ ID NO: 22). An artificial intron 5'-GTAAGTTTAAA-CATATATACTAACTAACCCATGGAT-TATTTAAATTTTCAG-3' (SEQ ID NO: 18) was inserted at position 264 with respect to the ATG.

a 300 bp fragment containing the glh-2 3'UTR (nt 3287 to 4087 with respect to glh-2 start codon) recovered form a 6.3 kb glh-2 genomic fragment subcloned in pBluescript KS (Stratagene) (M. E. Gruidl et al., *Proc. Natl. Acad. Sci. USA* 93:13837–13842 (1996); gift of Karen Bennett, University of Missouri).

The transgenic strain EG1643 that contains the Mos1 transposase expression vector has been generated by coinjection of lin-15(n765) worms with:

the Hind III-EcoRI fragment of pJL44 (injection concentration: 10 ng/µl)

the Eag I-Kpn I lin-15 genomic rescuing fragment from EKL15, S. L. McIntire et al., *Nature* 389:870–876 (1997)

the Pst I-BsiW I fragment of pPD97/98 that drives expression of the Green Fluorescent Protein in the coelomocytes (gift of Piali Sengupta, Brandeis University) (injection concentration: 10 ng/µl)

EcoRV-digested genomic DNA prepared from N2 worms (injection concentration: 80 ng/µl)

The resulting strain lin-15(ts); oxEx166[hsp::MosTase:.glh-2; pPD97198; lin-15(+)] has a wild-type phenotype. The presence of the extrachromosomal array causes expression of GFP in the coelomocytes which can be visualized using fluorescence microscopy.

Mobilization of the transposon in the *C. elegans* genome

Mobilization of Mos1 was achieved by crossing the transposase-expressing strain into worms containing the Mos1 transposon-containing array. lin-15(ts); oxEx166 [hsp:: MosTase:.-glh-2; pPD97198; lin-15(+)] hermaphrodites were crossed with N2 males at 25° C. Non-Muv males lin-15(ts); oxEx166 were crossed with lin-15(ts); oxEx164 [Mos1; rol-6(sd)] Rol non-Muv hermaphrodites previously grown at 15° C.

The cross was kept at 20° C. Late L4 larvae or young adult Rol worms were transferred to a fresh plate and heat-shocked for 1 hour at 35° C. After 6 hours, non-Muv Rol P0 animals (lin-15(ts); oxEx164; oxEx166) were transferred to a fresh plate and allowed to lay eggs for 48 hours. A fraction of the F1 animals contain insertions of Mos1 in their genome and can be screened for mutant phenotypes.

Identification of transposon insertion sites

Mos1 insertions were identified by inverse PCR, as shown in FIG. 3. Genomic DNA was prepared according to standard procedure. Approximately 100 ng of genomic DNA was digested by Sau3A in a 10 µl volume for 3 to 14 hours. The restriction enzyme was inactivated by heating for 20 minutes at 70° C. Fragments were circularized by self-ligation (overnight incubation at 15° C. with 5 units of T4 DNA ligase).

3 µl of ligated DNA was used for PCR amplification. A first round of amplification was performed using the primers oJL103 5'-TCTGCGAGTTGTTTTTGCGTTTGAG (SEQ ID NO: 3) and oJL114 5'-AAAGATTCAGAAGGTCGG-TAGATGGG (SEQ ID NO: 10) (30 cycles, 45 seconds at 94° C./1 minute at 60° C./1 minute 15 seconds at 72° C., magnesium chloride concentration: 1.5 mM). The product of the first amplification was diluted 100-fold and subjected to a second round of amplification using the nested primers oJL115 5'-GCTCAATTCGCGCCAAACTATG (SEQ ID NO: 11) and oJL116 5'-GAACGAGAGGCAGATG-GAGAGG (SEQ ID NO: 12) (25 cycles, 45 seconds at 94° C./1 minute at 62° C./1 minute 15 seconds at 72° C., magnesium chloride concentration: 2.5 mM). Resulting fragments were run on an agarose gel, gel-purified and sequenced either directly or after subcloning.

FIG. 4 contains the sequence of an inverse PCR product demonstrating insertion of Mos1 in chromosome X. Nucleotides in capital letters are from the Mos1 transposon. *C. elegans*-flanking genomic region is in lower case. It matches the Y47C4.Contig215 sequence from chromosome X available at the Sanger Centre.

Mos1, a mariner-like transposon isolated from *Drosophila mauritiana* was used. Transgenic worms containing Mos1 in an extrachromosomal array were crossed with transgenic worms containing an expression vector in which a heat-shock promoter (hsp 16-48) drives the expression of the mos transposase (FIG. 1). Cross-progeny containing both the Mos1 transposon and the mos transposase were isolated. Heat-shock of these worms induced the expression of the transposase which in turn caused Mos1 elements to transpose from the extrachromosomal array into the *C. elegans* genome. Five insertions were isolated, for a rate of one in seventeen animals analyzed. However, this array is only 20% stable per generation. Thus, there in on average one transposition into chromosomes for every three germ cells exposed to the transposon.

Some insertions will disrupt genes and cause mutant phenotypes. Mutant worms are outcrossed with wild-type worms containing no Mos1 transposon. Since the insertion responsible for the mutation cosegregates with the mutant phenotype, it is possible to isolate the single relevant Mos1 insertion after only a few outcrosses. Genomic DNA is then prepared from the outcrossed mutant. Regions flanking the transposon are recovered by inverse PCR and sequenced. Comparison of flanking sequences with the *C. elegans* genome sequence allows immediate identification of the mutated gene. This new mutagenesis system will significantly speed up the identification of genes of interest using *C. elegans* as a genetic model.

Example 9

Mos1 Mutagenesis and Rapid Cloning of Genes

In one embodiment, the method described in this invention is capable of generating mutations which can be rapidly cloned based on the Mos1 unique DNA tag. To demonstrate that this is true, mutants have been identified and the relevant genes have been cloned using inverse PCR. Specifically, a morphological mutant in *C. elegans* was isolated which causes the worms to be short and squat. Such mutations are called dumpy mutations and are given the three letter designation "dpy". A dumpy animal was identified after mobilization of the wild-type Mos1 transposon. DNA was prepared, cleaved with the restriction enzyme Sau3A, and religated. Inverse PCR was performed using primers contained within the transposon but facing outward. The amplified fragment was sequenced. The Mos1 element was inserted 175 nucleotides 5' of F54D8.1, which encodes a collagen protein. An inspection of the genetic map demonstrated that this insertion is in a chromosomal interval which also contains the dpy-17 gene which had been previously defined by point mutations using chemical mutagens by Sydney Brenner in 1974. A complementation test was performed and the test demonstrated that this mutation was an allele of dpy-17. Thus, the method is capable of rapidly demonstrating the molecular identity of a gene which had remained unknown for almost 30 years. Mutants incapable of detecting high osmotic gradients (Osm) were also screened for. The first Osm mutant identified was cloned in a similar manner and proved to be an insertion of Mos1 in exon 10 of the eat-4 gene.

Example 10

Targets of Transposase and Transposon

For Mos1 insertions to be useful for the cloning of mutated genes, the transposase must specifically mobilize Mos1 and not other mariner elements. The C. elegans genome contains endogenous transposons. Apart from the most active Tc1 and Tc3 transposons, which are distantly related to Mos1, every haploid genome contains at least 55 copies of a Mariner Like Element (MLE), which is closely related to Mos1. M. M. Sedensky, S. J. Hudson, B. Everson, P. G. Morgan, *Nucleic Acids Res.* 22, 1719 (1994); H. M. Robertson, D. J. Lampe, *Mol. Biol. Evol.* 12, 850 (1995). Since in a few cases transposases of the Mariner family have been shown to cross-mobilize distinct but related transposons (P. Sundararajan, P. W. Atkinson, D. A. O'Brochta, *Insect Mol. Biol.* 8, 359 (1999)), it was tested whether *Mos* transposase expression had triggered transposition of the endogenous MLEs. Eight strains in which Mos1 insertions had occurred were analyzed by Southern blot for changes in MLE distribution. No changes in MLE distribution were detected. Worm genomic DNA of lin-15(n 765) and Mos1-containing strains was extracted, Bgl II digested and run for Southern blot analysis using standard procedures. Oligos oJL132: 5'-ATATGCGGTGCGATGGGTGAG (SEQ ID NO: 8) and oJL133: 5'-GGCGAACGCGATGAGAAGAAAG (SEQ ID NO: 9) were used to amplify a 842 bp MLE fragment from N2 worm genomic DNA. The PCR product was sequenced and used for probe synthesis (data not shown), indicating that *Mos* transposase is specific for Mos1 in the *C. elegans* germline.

Figure 7A:
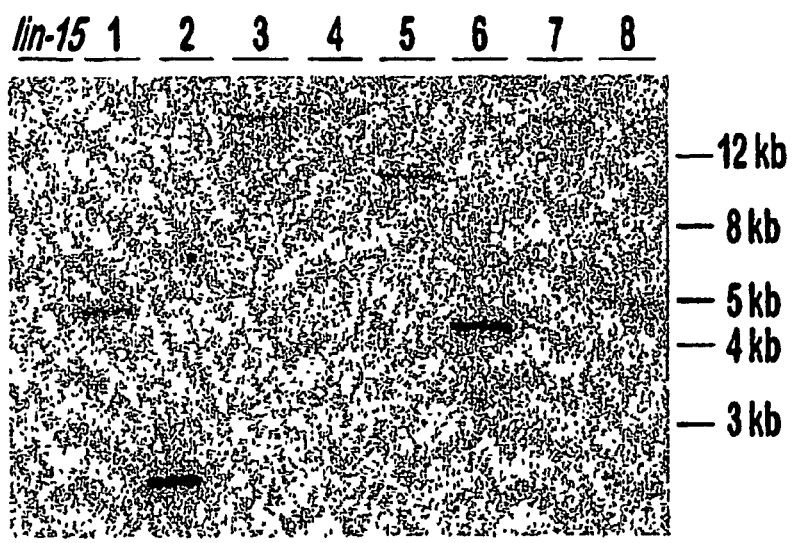
Figure 7B:
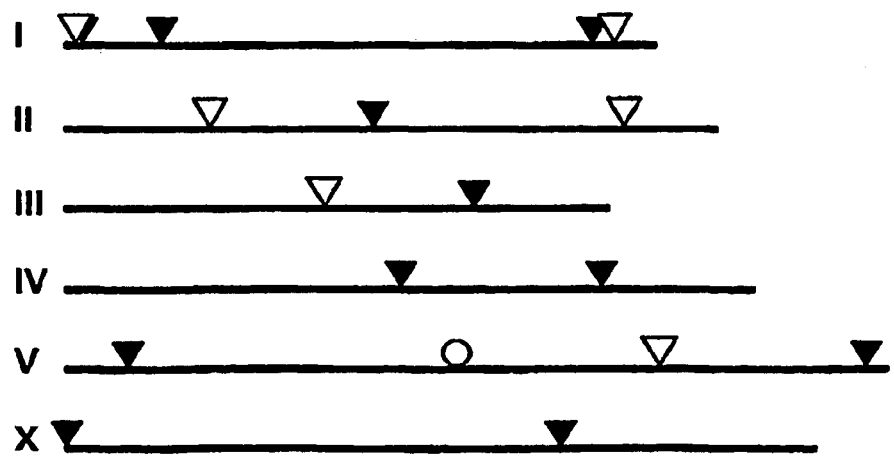

How many insertions occurred in every animal and what were their distributions? The number of chromosomal insertions per strain was determined by Southern blot analysis in eight insertion strains. Only one insertion per strain was detected (FIG. 7A). To determine the location of the mobilized transposons, the left junctions of 17 insertions were cloned using inverse PCR. Approximately 100 ng of total genomic DNA was digested with Sau3A, self-ligated under dilute conditions, and then 3% of the ligation was subjected to two rounds of nested PCR using the following primers: oJL103 (SEQ ID NO: 3)/oJL114 5'-AAAGATTCAGAAGGTCGGTAGATGGG (SEQ ID NO: 10) (first PCR), oJL115 5'-GCTCAATTCGCGCCAAACTATG (SEQ ID NO: 11)/ oJL116 5'-GAACGAGAGGCAGATGGAGAGG (SEQ ID NO: 12) (second PCR). PCR products were purified on agarose gel and sequenced using oJL115 (SEQ ID NO: 11) as a primer. In agreement with the Southern blot experiments, only one insertion per strain was detected. Insertion sites were distributed on all six chromosomes (FIG. 7B). Transposition occurred into exons, introns and intergenic regions (Table 2). Sequences flanking both sides of the transposon were determined for nine of the localized insertions. In each case, the inverted terminal repeats were complete and flanked by a TA dinucleotide that arose from the duplication of the original TA found in the genomic sequence (FIG. 7C).

Table 2. Properties of Mos1 genomic insertions. Mos1 flanking were compared with the *C. elegans* genome sequence. Physical location in the genome is given as the nucleotide position of the corresponding clone in the *C. elegans* database (ACeDB).

| Isolation name | Transposon source | Physical location | Interpolated genetic location | Genefinder predictions |
|---|---|---|---|---|
| oxTi1 | Extra-chromosomal | Y65B4BL @ 27,362 | LGI, −19 | Intergenic |
| oxTi2 | Extra-chromosomal | Y44E3A @ 34,440 | LGI, −4.75 | Intergenic |
| oxTi3 | Extra-chromosomal | M01E5 @ 19,740 | LGI, +29.9 | Intergenic |
| oxTi4 | Extra-chromosomal | T13C2 @ 4,948 | LGII, +0.1 | Exon #4 of F41G.12 |
| oxTi5 | Extra-chromosomal | K08E5 @ 31,631 | LGIII, +4.61 | Intergenic |
| oxTi6 | Extra-chromosomal | H23L24 @ 4,529 | LGIV, +3.9 | Intergenic |
| oxTi7 | Extra-chromosomal | K08D8 @ 4234 | LGIV, +6.6 | Intergenic |
| oxTi8 | Extra-chromosomal | R09B5 @ 22,929 | LGV, −19.0 | Exon #6 of R09B5.12 |
| oxTi9 | Extra-chromosomal | Y69H2 @ 39,771 | LGV, +17.49 | Intron #5 of Y69H2.4 |
| oxTi10 | Extra-chromosomal | Y47C4A | LGX, −20 | Repeat |
| oxTi11 | Extra-chromosomal | C34E11 @ 12,022 | LGX, +6.55 | Exon #10 of C34E11.1 |
| oxTi12 | Integrated array | Y71A12B @ 50,370 | LGI, +21 | Intergenic |
| oxTi13 | Integrated array | Y48G1C @ 19,916 | LGI, −19.8 | Intergenic |
| oxTi14 | Integrated array | C17F4 @ 22,793 | LGII, −8.06 | Exon #18 of gcy-19 |
| oxTi15 | Integrated array | F35C5 @ 5,735 | LGII, +10 | Intergenic |
| oxTi16 | Integrated array | C06B3 @ 14,747 | LGV, +5.79 | Intergenic |
| oxTi17 | Integrated array | R01H2 @ 20,193 | LGIII, −0.86 | Intergenic |

Comparison of the insertion site sequences did not reveal a strong consensus motif for the target DNA. Molecular analysis of the insertions therefore demonstrated that Mos1 insertion obeyed properties previously observed for mariner class transposons. However, a formal possibility remained that Mos1 hopped into the genomic DNA present in one of the extrachromosomal arrays and that recombination occurred subsequently between the array and the genome. To rule out this possibility, the insertion oxTi4 which was positioned 35 kb away from snt-1 was genetically mapped. In agreement with this physical location, oxTi4 was mapped less than 2.5 map units from snt-1: 20 Snt-1 individuals were cloned from the self-progeny of oxTi4/snt-1 hermaphrodites. None of the mutants segregated oxTi4. The presence of oxTi4 was determined by PCR using one Mos1 primer pointing towards the right end of the transposon (oJL89 (SEQ ID NO: 5)) and one primer in the genome (oJL129 5'-CCAAATGCGTCTGTCCCACTC (SEQ ID NO: 13)). A PCR positive control was performed on each DNA sample using cha-1 primers.

Example 11

Remobilization of a Genomic Transposon Insertion

The transposition events documented above were all excisions from an array of transposons residing in *Drosophila* DNA. To determine whether the transposase acts on a single Mos1 transposon in a *C. elegans* chromosome, the oxTi4 insert was remobilized. Primers for PCR were designed flanking the oxTi4 insertion. A first PCR round was performed with primers located 1671 nt upstream and 3144 bp downstream to oxTi4 (respectively oJL149 5'-AAG-TATGGCCAAACGACCCGACAC (SEQ ID NO: 14) and oJL150 5'-GCATTGGCACCTTTCTCCCTTCT (SEQ ID NO: 15)). A second round was performed using primers 493 bp upstream and 913 downstream to oxTi4 (respectively oJL145 5'-ACAGGCAGCATTTTGTAGTCT (SEQ ID NO: 16) and oJL148 5'-AGGCTGCCTCGTAAGTTCCTACAG (SEQ ID NO: 17)). Short PCR products were gel purified, subcloned and sequenced. The transposase-expressing transgene (oxEx167[glh-2:Transposase]) was crossed into animals homozygous for the oxTi4 insertion and DNAs from the progeny were analyzed for amplified fragments shorter than the insertion. These shorter PCR products represented a variety of excision events, including the three nucleotide excision footprint previously characterized for Mos1 excisions (G. Bryan, D. Garza, D. Hartl, *Genetics* 125, 103 (1990)), as well as smaller footprints, excisions and even incomplete excisions (Table 3). Since these products could arise from excision events in somatic cells, progeny animals that lost the transposase expression array were analyzed. Pools of 15 individuals from oxTi4; oxEx167[glh-2:Transposase] progeny that lost the transposase array were transferred to fresh plates and allowed to lay eggs for 24 hours. Adult worms were then analyzed by a single round of PCR using the primers oJL145 (SEQ ID NO: 16)-oJL148 (SEQ ID NO: 17). Sixty individuals were cloned from the progeny of the pool exhibiting short PCR product and analyzed at the next generation to identify clones that lost oxTi4. One animal was identified among 954 progeny in which excision of the transposon had occurred. In this animal the excision left a 3 bp footprint and the duplicated TA dinucleotide which together resulted in a +2 frameshift. These data indicate that single copies of the Mos1 *Drosophila* transposon can excise from *C. elegans* DNA in the germline to introduce frameshift or deletion mutations at the transposon insertion site.

Table 3. Lesions generated by excision of the oxTi4 insert. The extrachromosomal [glh-2:Transposase] transgene was crossed into animals homozygous for the oxTi4 insertion. PCR was used to analyze the oxTi4 insertion site after the loss of Mos1. Pools of 15 individuals from oxTi4; oxEx167 [glh-2:Transposase] progeny that lost the transposase array were transferred to fresh plates and allowed to lay eggs for 24 hours. Adult worms were then analyzed by a single round of PCR using the primers oJL145 (SEQ ID NO: 16)-oJL148 (SEQ ID NO: 17). Sixty individuals were cloned from the progeny of the pool exhibiting short PCR product and analyzed at the next generation to identify clones that lost oxTi4. Top line: sequence of oxTi4. Lower case: Mos1 sequence. Upper case: genomic sequence. Bold: TA dinucleotide duplicated during Mos1 insertion. Bottom lines: excision products. Dash: deleted base pairs. The insertion (bottom line, italic letters) corresponds to an internal fragment of Mos1 (nt 147 to 178).

```
CTCTTTTCCAGACGAGTAccaggtgtac . . . tacacctgaTATATCCTTTTGTTCCTT (SEQ ID NOS:
47 and 48)
CTCTTTTCCAGACGAGTA - - - TATATCCTTTTGTTGCTT (SEQ ID NO:49
CTCTTTTCCAGACGAGTA - - - aTATATCCTTTTGTTCCTT (SEQ ID NO:50)
CTCTTTTCCAGACGAGTA - - - tgaTATATCCTTTTGTTCCTT (SEQ ID NO:51)
CTCTTTTCCAGACGAGTAc - - - TATATCCTTTTGTTCCTT (SEQ ID NO:52)
- - - 249 bp deletion - - - tgaTATATCCTTTTGTTCCTT (SEQ ID NO:53)
CTCTTTTCCAGACGAGa - - - 143 bp deletion - - - (SEQ ID NO:54)
CTCTTTTCCAGACGAGTA - - - 188 bp deletion - - - (SEQ ID NO:55)
- - - 463 bp deletion - - -
CTCTTTTCCAGACGAGTAattgtttactctcagtgcagtcaacatgtcgaTATCCTTTTGTTCCTT
(SEQ ID NO:56)
```

Example 12

Engineering Mutations in the *C. elegans* Genome by Transgene Instructed DNA Double Strand Break Repair Following Mos1 Excision Germline expression of the Mos transposase under the control of the glh-2 promoter causes reexcision of single copies of Mos1 inserted in the *C. elegans* genome. Remobilization of the transposon causes a DNA double strand break (DSB) at the site of excision which is repaired by the cellular machinery. In 1992, R. Plasterk and J. Groenen (*EMBO J.* 11:287) demonstrated that a DSB caused by excision of a Tc1 transposon in a mut-6(st702) background can be repaired using DNA contained in an extrachromosomal array that carries sequences homologous to the region of excision. As a result, sequences flanking the break can be replaced by sequences contained in the transgene. This strategy provides a way to engineer mutations in the genome. However, this approach never became a routine strategy probably because transposition is not controlled and excision occurs at low rates in such mutant strains.

The controlled transposition of Mos1 provides an efficient tool to use this strategy for engineering of the *C. elegans* genome: after a Mos1 insertion has been identified in the gene of interest, a transgene is constructed with mutated sequences homologous to the region of insertion. The transgene that carries the glh-2::Mos transposase expression vector is crossed into the strain that contain the Mos1 genomic insertion and the template transgene. Expression of Mos transposase causes Mos1 excision and the progeny is screened by PCR for transgene instructed repair at the excision site (FIG. 8).

The feasibility of regulated mobilization of a heterologous transposon in the *C. elegans* germline was thus demonstrated. The characteristics of Mos1 transposition suggest that it could be used as a technique for tagging mutant genes. First, the Mos transposase does not activate transposition of endogenous transposons. Second, transposition of Mos in the germline is strictly dependent on the expression of the transposase. In this respect, the use of a heat-shock promoter to express the transposase is of particular interest since it provides a convenient way to turn transposition on and off and to stabilize new inserts. Third, insertion sites of Mos1 in the genome do not exhibit strong sequence bias. Transposons were inserted into exons, introns and intergenic regions. Comparison of the insertion sites did not reveal a strong consensus sequence apart from the TA dinucleotide. Fourth, excision and insertion frequencies can be differentially manipulated by expressing the transposase under the control of different promoters. The heat-shock promoter caused very low rates of excision and loss of the transposon array but high rates of transposon insertion. The glh-2 promoter construct caused a low rate of insertion but a high rate of excision and loss of the transposon array. Since transposon insertions frequently do not disrupt gene function in *C. elegans* even if the insertion occurs in an exon (A. M. Rushforth, B. Saari, P. Anderson, *Mol. Cell. Biol.* 13, 902 (1993); A. M. Rushforth, P. Anderson, *Mol. Cell. Biol.* 16, 422 (1996)), transposons are usually remobilized to generate deletion alleles (D. Eide, P. Anderson, *Mol. Cell. Biol.* 8, 737 (1988); R. R. Zwaal, A. Broeks, J. van Meurs, J. T. Groenen, R. H. Plasterk, *Proc. Natl. Acad. Sci. USA* 90, 7431 (1993)). It was thus demonstrated that the glh-2 expression construct can be used to generate deletion alleles of the genes containing Mos1 insertions.

Mos1 transposition in *C. elegans* will allow the development of two new genetic tools. First, mutations identified in forward screens using Mos1 will allow the rapid cloning of the mutated gene. Second, a library of insertions localized in the genome could be generated; the glh-2 expression construct could then be used to remobilize these insertions at high frequency and generate deletion and frameshift mutations in genes of interest.

The invention claimed is:

1. A method of transposon-mediated mutagenesis in a *C. elegans* genome, comprising:
   a. introducing a transgene construct into the *C. elegans* genome, wherein the construct comprises a transposase gene which is operably linked to a regulable expression control element and a 3' untranslated region of a gene that is expressed in the *C. elegans* germline, wherein the 3' untranslated region comprises a glh-2 3' untranslated region; and
   b. expressing the transposase gene, such that a transposon in the *C. elegans* genome transposes, causing a mutation in the *C. elegans* germline.

2. The method of claim 1, wherein the transposon comprises a heterologous transposon.

3. The method of claim 2, wherein the heterologous transposon is introduced into the *C. elegans* genome.

4. The method of claim 2, wherein the transposon comprises a Mos 1 transposon.

5. The method of claim 2, wherein the transposase gene comprises restriction sites 5' of the start codon, restriction sites 5' of the stop codon, and an artificial intron in the transposase gene open reading frame.

6. The method of claim 2, wherein the regulable expression control element is an inducible promoter.

7. The method of claim 6, wherein the promoter comprises a heat-shock promoter.

8. The method of claim 6, wherein the promoter comprises a tetracycline-regulated promoter.

9. The method of claim 2, wherein the construct is substantially free of bacterial plasmid DNA sequences.

10. The method of claim 2, wherein the construct is substantially free of repeated DNA sequences.

11. The method of claim 2, wherein the regulable expression control element comprises a glh-2 promoter.

12. The method of claim 1, wherein the transposon comprises an endogenous transposon.

13. The method of claim 12, wherein the transposon comprises a Tc3 transposon.

14. The method of claim 13, wherein the transposase gene is a TC3A transposase gene.

15. The method of claim 12, wherein the regulable expression control element is an inducible promoter.

16. The method of claim 15, wherein the promoter comprises a heat-shock promoter.

17. The method of claim 15, wherein the promoter comprises a tetracycline-regulated promoter.

18. The method of claim 1, wherein the transposase gene is a TC3A transposase gene.

19. The method of claim 1, wherein the construct is substantially free of bacterial plasmid DNA sequences.

20. The method of claim 1, wherein the construct is substantially free of repeated DNA sequences.

21. The method of claim 1, wherein the regulable expression control element comprises a heat-shock promoter.

22. The method of claim 1, wherein the regulable expression control element comprises a glh-2 promoter.

23. The method of claim 1, further comprising introduction of one or more additional copies of an endogenous transposon into the *C. elegans* germline.

24. The method of claim 23, wherein the endogenous transposon is a Tc3 transposon.

* * * * *

UNITED STATES PATENT AND TRADEMARK OFFICE
CERTIFICATE OF CORRECTION

| | | |
|---|---|---|
| PATENT NO. | : 7,196,244 B1 | Page 1 of 1 |
| APPLICATION NO. | : 09/980644 | |
| DATED | : March 27, 2007 | |
| INVENTOR(S) | : Jean-Louis Bessereau and Erik M. Jorgensen | |

It is certified that error appears in the above-identified patent and that said Letters Patent is hereby corrected as shown below:

In the Specification

Insert the following heading and paragraph to Column 1, immediately prior to the "FIELD OF INVENTION" heading:

--STATEMENT REGARDING FEDERALLY SPONSORED RESEARCH OR DEVELOPMENT

This invention was made with government support under Grant No. MCB9733685 awarded by the National Science Foundation. The government has certain rights in the invention.--

Signed and Sealed this
Twenty-first Day of October, 2014

Michelle K. Lee
*Deputy Director of the United States Patent and Trademark Office*